(12) United States Patent
Blumberg et al.

(10) Patent No.: US 8,962,646 B2
(45) Date of Patent: Feb. 24, 2015

(54) PERIPHERALLY ACTING OPIOID COMPOUNDS

(75) Inventors: Laura Cook Blumberg, Lincoln, MA (US); Derrick Arnelle, Arlington, MA (US)

(73) Assignee: Alkermes, Inc., Waltham, MA (US)

( * ) Notice: Subject to any disclaimer, the term of this patent is extended or adjusted under 35 U.S.C. 154(b) by 0 days.

(21) Appl. No.: 13/537,544

(22) Filed: Jun. 29, 2012

(65) Prior Publication Data

US 2013/0005755 A1    Jan. 3, 2013

Related U.S. Application Data

(60) Provisional application No. 61/502,721, filed on Jun. 29, 2011.

(51) Int. Cl.
| | | |
|---|---|---|
| *A61K 31/505* | (2006.01) | |
| *A61K 31/44* | (2006.01) | |
| *C07D 471/00* | (2006.01) | |
| *C07D 491/00* | (2006.01) | |

(Continued)

(52) U.S. Cl.
CPC ............ *C07D 489/02* (2013.01); *C07D 471/08* (2013.01)
USPC ............. 514/282; 514/274; 514/289; 546/44; 546/45; 546/46; 546/74

(58) Field of Classification Search
CPC .. C07D 471/00; C07D 491/00; C07D 498/00; C07D 513/00; C07D 515/00; A61K 31/44
See application file for complete search history.

(56) References Cited

U.S. PATENT DOCUMENTS

| 3,856,795 A | 12/1974 | Yardley |
| 3,957,793 A | 5/1976 | Wentland et al. |

(Continued)

FOREIGN PATENT DOCUMENTS

| DE | 2254298 | 5/1974 |
| EP | 0254120 A2 | 1/1988 |

(Continued)

OTHER PUBLICATIONS

Sintim, HO. et al. Conservative Change to the Phosphate Moiety of Cyclic Diguanylic Monophosphate Remarkably Affects Its Polymorphism and Ability to Bind DGC, PDE, and PilZ Proteins. JACS. 2011, vol. 133, p. 9321.*

(Continued)

*Primary Examiner* — Rita Desai
*Assistant Examiner* — Ben S Michelson
(74) *Attorney, Agent, or Firm* — Elmore Patent Law Group, P.C.; Carolyn S. Elmore; Roy P. Issac

(57) ABSTRACT

The invention relates to a compound of Formula I, II, III, IV or a pharmaceutically acceptable ester or prodrug thereof:

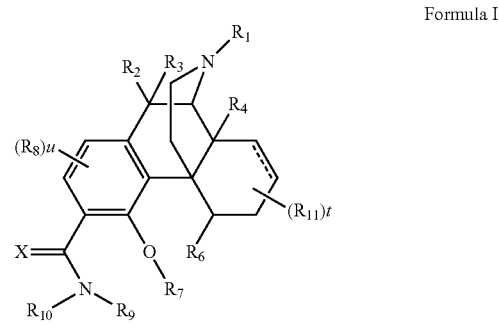

Formula I

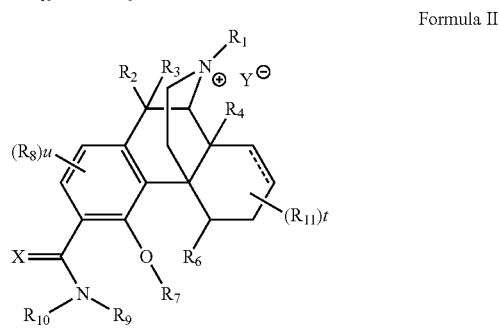

Formula II

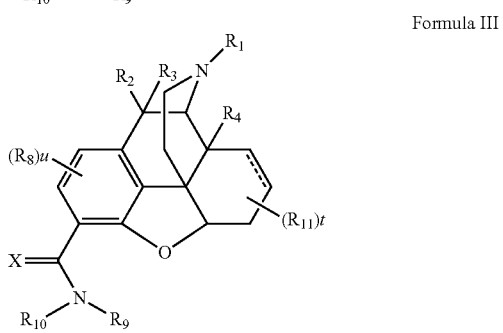

Formula III

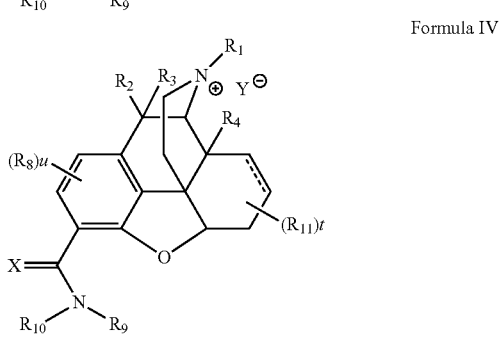

Formula IV

8 Claims, 5 Drawing Sheets

(51) Int. Cl.

| | |
|---|---|
| C07D 498/00 | (2006.01) |
| C07D 513/00 | (2006.01) |
| C07D 515/00 | (2006.01) |
| C07D 489/00 | (2006.01) |
| C07D 489/08 | (2006.01) |
| C07D 221/22 | (2006.01) |
| C07D 221/28 | (2006.01) |
| C07D 489/02 | (2006.01) |
| C07D 471/08 | (2006.01) |

(56) References Cited

U.S. PATENT DOCUMENTS

| | | | |
|---|---|---|---|
| 4,032,529 | A | 6/1977 | Wentland et al. |
| 4,176,186 | A | 11/1979 | Goldberg et al. |
| 4,205,171 | A | 5/1980 | Albertson |
| 4,374,139 | A | 2/1983 | Mohacsi |
| 4,464,378 | A | 8/1984 | Hussain |
| 4,489,079 | A | 12/1984 | Giudice et al. |
| 4,649,200 | A | 3/1987 | Portoghese |
| 4,929,622 | A | 5/1990 | Allen et al. |
| 5,258,386 | A | 11/1993 | Newman |
| 5,607,941 | A | 3/1997 | Merz et al. |
| 6,365,594 | B1 | 4/2002 | Dondio et al. |
| 6,784,187 | B2 | 8/2004 | Wentland |
| 6,812,236 | B2 | 11/2004 | Gibson et al. |
| 6,887,998 | B2 | 5/2005 | Wentland |
| 6,900,227 | B2 | 5/2005 | Alanine et al. |
| 7,262,298 | B2 | 8/2007 | Wentland |
| 7,265,226 | B2 | 9/2007 | Wentland |
| 7,439,239 | B2 | 10/2008 | Coats et al. |
| 7,553,850 | B2 | 6/2009 | Dax et al. |
| 7,557,119 | B2 | 7/2009 | Wentland |
| 7,582,650 | B2 | 9/2009 | DeCorte et al. |
| 7,956,187 | B2 | 6/2011 | Wentland |
| 8,026,252 | B2 | 9/2011 | Wentland |
| 8,252,929 | B2 | 8/2012 | Wentland |
| 2002/0099216 | A1 | 7/2002 | Gibson et al. |
| 2003/0187009 | A1 | 10/2003 | Wentland |
| 2005/0176645 | A1 | 8/2005 | Mickle et al. |
| 2005/0182258 | A1 | 8/2005 | Schmidhammer et al. |
| 2005/0215799 | A1 | 9/2005 | Wentland et al. |
| 2006/0030580 | A1 | 2/2006 | Wentland |
| 2006/0063792 | A1 | 3/2006 | Dolle et al. |
| 2007/0021457 | A1 | 1/2007 | Wentland |
| 2007/0238748 | A1 | 10/2007 | Wentland |
| 2008/0009478 | A1 | 1/2008 | Smith et al. |
| 2009/0197905 | A1 | 8/2009 | Wentland |
| 2009/0247562 | A1 | 10/2009 | Wentland |
| 2010/0130512 | A1 | 5/2010 | Wentland |
| 2010/0190817 | A1 | 7/2010 | Wentland |
| 2011/0230511 | A1* | 9/2011 | Wentland ............ 514/282 |
| 2011/0306603 | A1 | 12/2011 | Wentland |
| 2012/0302591 | A1 | 11/2012 | Wentland |

FOREIGN PATENT DOCUMENTS

| | | |
|---|---|---|
| EP | 0632041 A1 | 1/1995 |
| ES | 2121553 A1 | 11/1998 |
| GB | 874217 | 8/1961 |
| GB | 1340720 | 12/1973 |
| JP | 40010154 B4 | 5/1965 |
| WO | 93/11761 A1 | 6/1993 |
| WO | 97/25331 A1 | 7/1997 |
| WO | 98/52929 A1 | 11/1998 |
| WO | 0112197 A1 | 2/2001 |
| WO | 0137785 A2 | 5/2001 |
| WO | 02/36573 A2 | 5/2002 |
| WO | 03/101963 A1 | 12/2003 |
| WO | 2004005294 A2 | 1/2004 |
| WO | 2004007449 A1 | 1/2004 |
| WO | 2004045562 A2 | 6/2004 |
| WO | 2006052710 A1 | 5/2006 |
| WO | 2006096626 A3 | 9/2006 |
| WO | 2007014137 A | 2/2007 |
| WO | 2007014137 A2 | 2/2007 |
| WO | 2007022535 A3 | 2/2007 |
| WO | 2008144394 A2 | 1/2008 |
| WO | WO 2009/023567 A1 * | 2/2009 |
| WO | WO 2009023567 A1 * | 2/2009 |
| WO | 2010011619 A1 | 1/2010 |
| WO | 2011119605 A2 | 9/2011 |
| WO | WO 2011/230511 A1 * | 9/2011 |

OTHER PUBLICATIONS

Carey, FA. Organic Chemistry 6th Ed. McGraw Hill. 2006, chapter 1, p. 9.*
International Search Report and Written Opinion—PCT Application No. PCT/US09/051200 filed Jul. 21, 2009.
Vanalstine, M., Design, Synthesis and Evalulation of Novel n-substituted Derivatives of 8-Carboxamidocyclazocine Thesis (Ph.D.)—Rensselaer Polytechnic Institute, May 2007, pp. i-202, Jul. 9, 2009.
Wentland, et al., "Redefining the Structure-Activity Relationships of 2,6-methano-3-benzazocines.4. Opioid Receptor Binding Properties of 8[N-(4'-phenyl)-phenethyl) carboxamidol] Analogues of Cyclazocine and Ethylketocyclazocine," Journal of Medicinal Chemistry, vol. 49, No. 18, pp. 5635-5639 XP002550099 (Sep. 7, 2006).
Vanalstine, et al., "Redefining the Structure-Activity Relationships of 2,6-methano-3-benzazocines.5. Opioid Receptor Binding Properties of [N-(4'-phenyl)-phenethyl) Analogues of 8-CAC," Bioorganic & Medicinal Chemistry Letters, Pergamon, Elsevier Science, GB. vol. 17, No. 23, pp. 6516-6520 XP022325927 (Nov. 2, 2007).
Zhang, et al., "10-Ketomorphinan and 3-Substituted 3-desoxymorphinan Analogues as Mixed κ and μ Opioid Ligands: Synthesis and Biological Evaluation of Their Binding Affinity at Opioid Receptors," J. Med. Chem. 47, pp. 165-174 (2004).
Wentland, et al., "3-Carboxamido Analogues of Morphine and Naltrexone: Synthesis and Opioid Receptor Binding Properties", Bioorg. Med. Chem. Ltrs. 11, pp. 1717-1721 (2001).
Wentland, et al., "8-Carboxamidocyclazocine Analogues: Redefining the Structure-Activity Relationships of 2,6 Methano-3benzazocines", Bioorg. Med. Chem. Ltrs, 11, pp. 623-626 (2001).
Davies, et al., "Palladium Catalysed Elaboration of Codeine and Morphine," J. Chem. Soc. Perkin Trans., 1 pgs, 1413-1420 (2001).
McCurdy, et al., "Investigation of Phenolic Bioisosterism in Opiates: 3-Sulfonamido Analogues of Naltrexone and Oxymorphone," Organic Letters, vol. 2, No. 6, pp. 819-821 (2000).
Kubota, et al., "Palladium-Catalyzed Cyanation of Hindered, Electron-Rich Aryl Inflates by Zinc Cyanide", Tetrahedron Ltrs. 39, 2907-2910 (1998).
Kubota, et al., "Synthesis and Biological Activity of 3-Substituted 3-Desoxynaltrindole Derivatives", Bioorg. Med. Chem. Ltrs. 8, 799-804 (1998).
Wentland, et al., "8-Aminocyclazocine Analogues: Synthesis and Structure-Activity Relationships", Bioorg. Med. Chem. Ltrs. 10, pp. 183-187 (2000).
Wentland, et al., "Selective Protection and Functionalization of Morphine: Synthesis and Opioid Receptor Binding Properties of 3-Amino 3-desoxymorphine Derivatives", J. Med. Chem. 43, pp. 3558-3565 (2000).
Danso-Danquah, et al., "Synthesis and σ Binding Properties of 1'-and 3'-Halo-and 1',3'-Dihalo-N-normetazocine Analogues," J. Med. Chem., 38, 2986-2989 (1995).
Diaz, et al., "SAR & Biological Evaluation of Novel trans-3,4-dimethyl-4-arylpiperidine Derivatives as Opioid Antagonists," Bioorganic & Medicinal Chemistry Letters 15, pp. 3844-3848 (2005).
Ida, H., "The Nonnarcotic Antitussive Drug Dimemorfan: A Review," Clinical Therapeutics, vol. 19, No. 2, pp. 215-231 (1997).
Morera, et al., "A Palladium-Catalyzed Carbonylative Route to Primary Amides," Tetrahedron Ltrs. 39, pp. 2835-2838 (1998).
Jendralla, et al., "Efficient Kg-Scale Synthesis of Thrombin Inhibitor CRC 220," Tetrahedron, vol. 51, No. 44, pp. 12047-12068 (1995).
Cacchi, et al., "Palladium-Catalyzed Carbonylation of Aryl Triflates," Tetrahedron Ltrs., 27, pp. 3931-3934 (1986).

(56) References Cited

OTHER PUBLICATIONS

Varma, et al., "Microwave-Accelerated Solvent-Free Synthesis of Thioketones, Thiolactones, Thioamides, Thionoesters, and Thioflavonoids," Organic Letters, vol. 1, No. 5, pp. 697-700 (1999).

Dorwald, F., Zaragoza "Side Reactions in Organic Synthesis," Wiley-VCH, Weinheim p. IX of Preface (2005).

International Preliminary Examination Report for PCT/US01/45581, date of completion Feb. 5, 2003.

International Search report for PCT/US01/45581, date of completion Jul. 30, 2002.

Wentland, Mark P., et al., "Syntheses and Opioid Receptor Binding Affinities of 8-Amino-2,6-methano-3-benzazocines," Journal of Medicinal Chemistry, 2003, pp. 838-849, vol. 46, No. 5.

Wentland, Mark P., et al., "Redefining the Structure-Activity Relationships of 2, 6-methano-3-benzazocines, Opioid Receptor Binding Properties of Cyclic Variants of 8-carboxamidocyclazocine," Bioorgranic & Medicinal Chemistry, 2008, pp. 5653-5664, vol. 16, No. 10.

International Search Report and Written Opinion of the International Searching Authority for PCT/US2008/063713, date of mailing May 28, 2009.

Wentland, Mark, et al., "Redefining the Structure-Activity Relationships of 2,6-methano-3-benzazocines. Part 3: 8-Thiocarboxamido and 8-thioformamido Derivatives of Cyclazocine," Bioorg. Med. Chem. Letters, 15(10), pp. 2547-2551 (2005).

Wentland, Mark., et al., "Synthesis and Opioid Receptor Binding Properties of Highly Potent 4-hydroxy Analogue of Naltrexone," Bioorg. Med. Chem. Ltrs. 15(8): pp. 2107-2110 (2005).

International Search Report from International Application No. PCT/US2006/028634, mailed Jan. 26, 2007.

International Search Report from International Application No. PCT/US2005/039911, date of completion Apr. 19, 2006.

International Search Report and Written Opinion from International Application No. PCT/US2008/072632, mailed Dec. 23, 2008.

International Search Report and Written Opinion from International Application No. PCT/US2011/029425, mailed Sep. 16, 2011.

Mohacsi, et al., "Acylmorphinans. A Novel Class of Potent Analgesic Agents," J. Med. Chem. 1985, 28, pp. 1177-1180.

Coop, et al., "Opioid Affinity and Selectivity of 4-Hydroxy-3-methoxyindolomorphinan Analogues Related to Naltrindole," J. Med. Chem. 1999, 42, pp. 1673-1679.

Coop, et al., "Direct and Simple Conversion of Codeine to Thebainon-A and Dihydrothebainone," Heterocycles, vol. 50, No. 1, pp. 39-42 (1999).

Neumeyer, et al., "Design and Synthesis of Novel Dimeric Morphinan Ligands for κ and μ Opioid Receptors," J. Med. Chem., 46, pp. 5162-5170 (2003).

Bianchi, et al., "Quaternary Narcotic Antagonists' Relative Ability to Prevent Antinociception and Gastrointestinal Transit Inhibition in Morphine-Treated Rats as an Index of Peripheral Selectivity," Life Sciences, 30(22): pp. 1875-1883 (1982).

Huidobro-Toro, et al., Comparative Study on the Effect of Morphine and the Opioid-Like Peptides in the Vas Deferens of Rodents: Species and Strain Differences, Evidence for Multiple Opiate Receptors, Life Sciences vol. 28, pp. 1331-1336 (1981).

Simpkins, et al., "Evaluation of the Sites of Opioid Influence on Anterior Pituitary Hormone Secretion Using a Quaternary Opiate Antagonist," Neuroendocrinology, 54(4): pp. 384-390 (1991).

Bianchetti, et al., "Quaternary Derivatives of Narcotic Antagonists: Stereochemical Requirements at the Chiral Nitrogen for in vitro and in vivo Activity," Life Sciences, 33(Suppl 1), pp. 415-418 (1983).

Written Opinion of International Application No. PCT/US2005/039911, completed Apr. 19, 2006.

IPRP for International Application No. PCT/US2006/028634, date of issuance Jan. 22, 2008.

Bhargava, H.N., "Synthesis of 2'-Amino-17-cyclopropylmethy1-6 7-dehydro-3, 14-dihy-droxy-4, 5alpha-epoxy-6,7:4',5'-thiazolomorphinan from Naltrexone[1]," J. Heterocyclic Chem., 34, pp. 1195-1203 (1997).

Black, et al., "The Role of the Side Chain in Determining Delta and Kappa-Affinity in C5 Substituted Analogues of Naltrindole," J. Med. Chem., 46, pp. 314-317 (2003).

* cited by examiner

PERIPHERALLY ACTING OPIOID COMPOUNDS

RELATED APPLICATION

This application claims the benefit of U.S. Provisional Application No. 61/502,721, filed on Jun. 29, 2011. The entire teachings of the above application are incorporated herein by reference.

TECHNICAL FIELD

This invention relates to peripherally acting opioid compounds useful as opioid receptor modulators.

BACKGROUND OF THE INVENTION

Opiates have been the subject of intense research since the isolation of morphine in 1805, and thousands of compounds having opiate or opiate-like activity have been identified. Many opioid receptor-interactive compounds including those used for producing analgesia (e.g., morphine) and those used for treating drug addiction (e.g., naltrexone) have been employed in human therapy. Almost all therapeutically useful opioids in the benzomorphan and morphinan classes have a phenolic hydroxyl group (OH) at a position which is numbered "8" in the numbering system used for 2,6-methano-3-benzazocines [e.g., cyclazocine and EKC (ethylketocyclazocine)] and which is numbered "3" in the numbering system used for morphinans (e.g., morphine). When the 3-hydroxyl group is replaced by a number of small, polar, neutral residues, such as carboxamide and thiocarboxamide groups, the adjacent 4-position may be substituted with a hydroxyl to produce compounds with high affinity for the opioid receptor. (Wentland M: WO 2009023567; WO 2010011619; U.S. Pat. Nos. 6,784,187; 6,887,998; 7,262,298; 7,557,119). Compounds that bind to such receptors are likely to be useful in the treatment of diseases modulated by opiate receptors for example, mediating analgesia, combating drug and opioid addiction, alcohol addiction, drug overdose, mental illness, compulsive behavior, bladder dysfunctions, neurogenic bladder, interstitial cystitis, urinary incontinence, premature ejaculation, inflammatory pain, peripherally mediated and neuropathic pain, cough, convulsions, lung edema, diarrhea, constipation, pruritus, cardiac disorders, cardioprotection, and cognitive, respiratory depression, irritable bowel syndrome and gastro-intestinal disorders, immunomodulation, binge eating, anorexia, hyperalgesia, dyskinesia, anti-psychotic induced weight gain and as anti-tumor agents.

The potent antinociceptive actions of classical opioids such as morphine are traditionally considered to be predominantly mediated centrally through an action at the supraspinal or spinal level. Antinociceptive effects have also been demonstrated to result after local application of opioids in the periphery, for example, in mouse writhing, and in rat models of inflammation or neuropathic pain. These effects have been attributed to opioid induced actions mediated by peripheral opioid receptors. Neuroanatomical, molecular and electrophysiological studies have shown that such receptors are expressed on peripheral terminals of sensory neurons where they can modulate both afferent and efferent neuronal functions, resulting in antinociception. (Furst et. al. J Pharmacol Exp Ther. 2005, 312(2), 609-18.). In addition, opioid receptors have been found on immune cells known to migrate into enteric tissues and the epithelial cells lining the gastrointestinal tract. As such, opioids interacting with peripheral opioid receptors without crossing the blood-brain barrier might be used as potent analgesics and are devoid of centrally mediated side effects are of interest in treating opioid mediated diseases.

SUMMARY

The invention relates to compounds of Formula I, II, III, IV or a pharmaceutically acceptable ester or prodrug thereof:

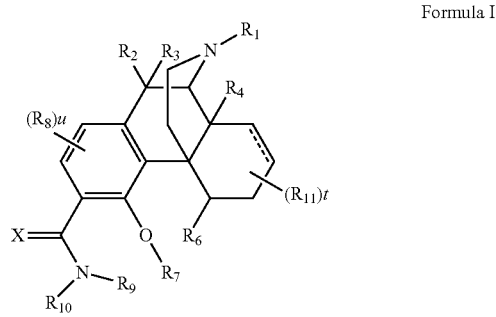

Formula I

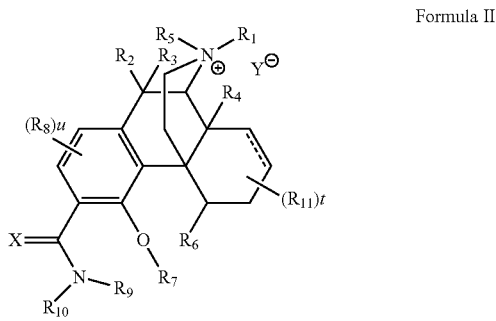

Formula II

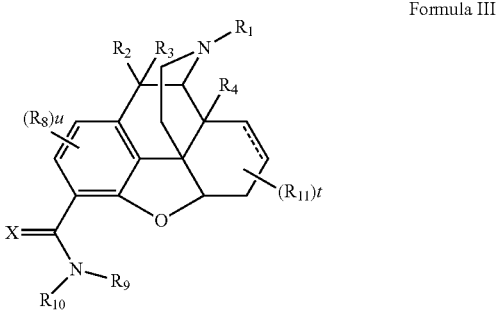

Formula III

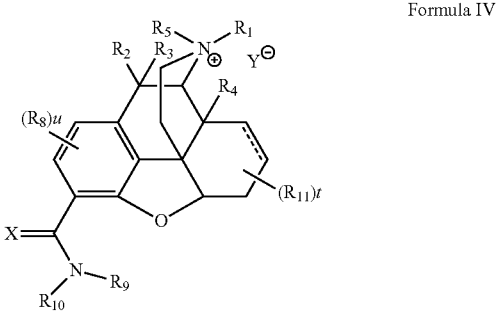

Formula IV

Wherein:
u is 0, 1 or 2;
t is 0, 1, 2, 3, 4, 5, 6, or 7;
X is S or O;
$Y^{\ominus}$ is a pharmaceutically acceptable counterion;
$R_1$ is selected from aliphatic, substituted aliphatic, aryl, substituted aryl, heterocyclyl or substituted heterocyclyl;

Each $R_2$, $R_3$, $R_4$, $R_6$, $R_8$, and $R_{11}$ is independently selected from absent, hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, alkylthio, substituted alkylthio, alkylsulfonyl, substituted alkylsulfonyl, aliphatic, substituted aliphatic, aryl, substituted aryl, heterocyclyl or substituted heterocyclyl; or alternatively, two of $R_2$, $R_3$, $R_4$, $R_8$ and $R_{11}$ together with the atoms they are attached to form one or two optionally substituted rings; alternatively $R_2$ and $R_3$ together with the carbon they are attached to form a C=X group or a vinyl group; alternatively, two $R_{11}$ groups together with the carbon atom to which they are attached form a C=X or a vinyl group;

wherein each $R_{20}$ and $R_{21}$ is independently selected from absent, hydrogen, halogen, -alkyl, substituted alkyl, aryl or substituted aryl;

$R_5$ is alkyl, substituted alkyl, aryl or substituted aryl;
$R_7$ is hydrogen, alkyl, substituted alkyl, aryl or substituted aryl;
$R_9$ is selected from hydrogen, aliphatic, substituted aliphatic, aryl, substituted aryl, heterocyclyl or substituted heterocyclyl
$R_{10}$ is selected from —$[C(R_{23})(R_{24})]_m$—$R_{25}$;

Wherein m is 0, 1, 2, 3, 4, 5, 6, 7, or 8;

Each $R_{23}$ and $R_{24}$ is independently selected from hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, alkylthio, substituted alkylthio, alkylsulfonyl, substituted alkylsulfonyl, aliphatic, substituted aliphatic, aryl, substituted aryl, heterocyclyl or substituted heterocyclyl; and, $R_{25}$ is heterocyclyl, substituted heterocyclyl, aryl substituted with heteroaryl or aryl substituted with heterocyclyl.

The invention further relates to a method of treating a disease or disorder by modulating the activity of an opioid receptor comprising the step of administering a compound of Formula I to a subject in need thereof.

DESCRIPTION OF FIGURES

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
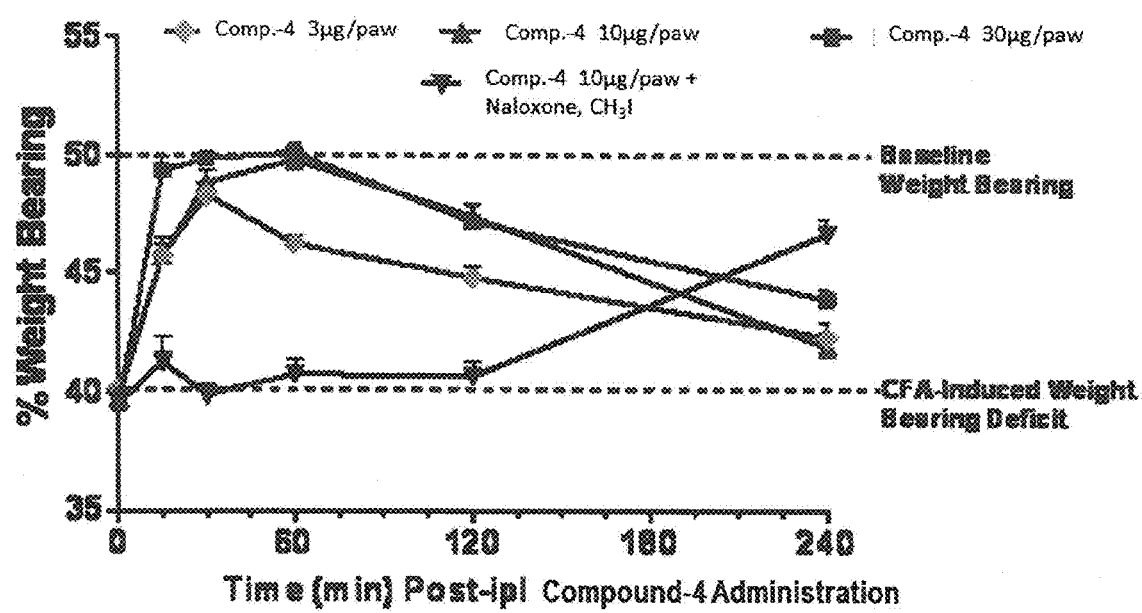
FIG. 1: The administration (intra-plantar) of Compound 4 produced a dose-dependent reversal of CFA-induced weight bearing deficits at 3, 10 and 30 μg/paw.

In one embodiment, the invention relates to a compound of Formula I, II, III, IV or a pharmaceutically acceptable ester or prodrug thereof:

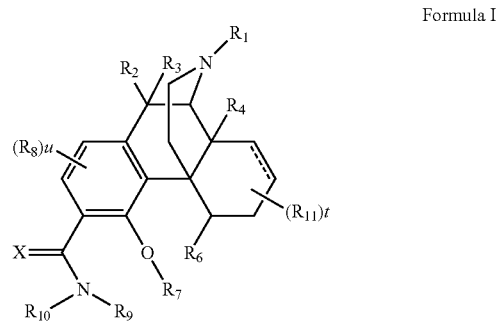

Formula I

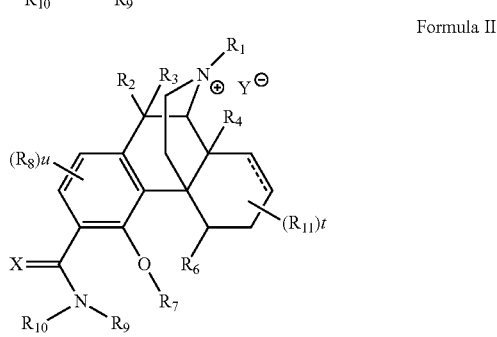

Formula II

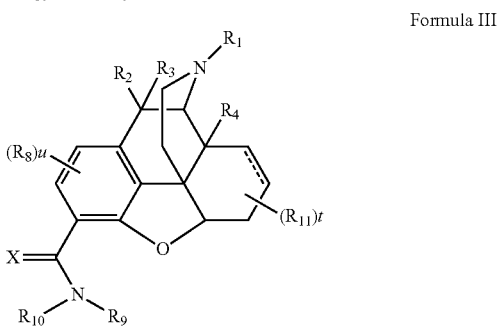

Formula III

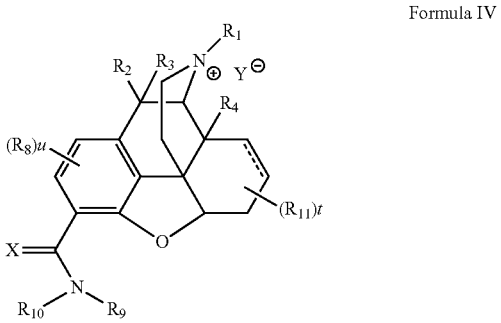

Formula IV

Wherein:
u is 0, 1 or 2;
t is 0, 1, 2, 3, 4, 5, 6, or 7;
X is S or O;
$Y^{\ominus}$ is a pharmaceutically acceptable counterion;

$R_1$ is selected from aliphatic, substituted aliphatic, aryl, substituted aryl, heterocyclyl or substituted heterocyclyl;

Each $R_2$, $R_3$, $R_4$, $R_6$, $R_8$, and $R_{11}$ is independently selected from absent, hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, alkylthio, substituted alkylthio, alkylsulfonyl, substituted alkylsulfonyl, aliphatic, substituted aliphatic, aryl, substituted aryl, heterocyclyl or substituted heterocyclyl; or alternatively, two of $R_2$, $R_3$, $R_4$, $R_8$ and $R_{11}$ together with the atoms they are attached to form one or two optionally substituted rings; alternatively $R_2$ and $R_3$ together with the carbon they are attached to form a C=X group or a vinyl group; alternatively, two $R_{11}$ groups together with the carbon atom to which they are attached form a C=X or a vinyl group;

wherein each $R_{20}$ and $R_{21}$ is independently selected from absent, hydrogen, halogen, -alkyl, substituted alkyl, aryl or substituted aryl;

$R_5$ is alkyl, substituted alkyl, aryl or substituted aryl;

$R_7$ is hydrogen, alkyl, substituted alkyl, aryl or substituted aryl;

$R_9$ is selected from hydrogen, aliphatic, substituted aliphatic, aryl, substituted aryl, heterocyclyl or substituted heterocyclyl;

$R_{10}$ is selected from —$[C(R_{23})(R_{24})]_m$—$R_{25}$;

Wherein m is 0, 1, 2, 3, 4, 5, 6, 7, or 8;

Each $R_{23}$ and $R_{24}$ is independently selected from hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, alkylthio, substituted alkylthio, alkylsulfonyl, substituted alkylsulfonyl, aliphatic, substituted aliphatic, aryl, substituted aryl, heterocyclyl or substituted heterocyclyl; and, $R_{25}$ is heterocyclyl, substituted heterocyclyl, aryl substituted with heteroaryl or aryl substituted with heterocyclyl.

The invention further relates to a method of treating a disease or disorder by modulating the activity of an opioid receptor(s) comprising the step of administering a compound of Formula I or II to a subject in need thereof.

In a preferred embodiment, the invention relates to a compound of Formula V, VI, or a pharmaceutically acceptable ester or prodrug thereof:

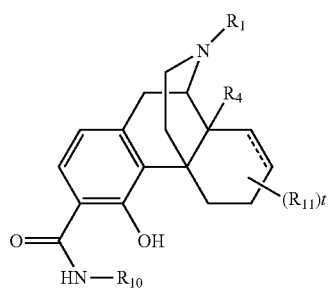

Formula V

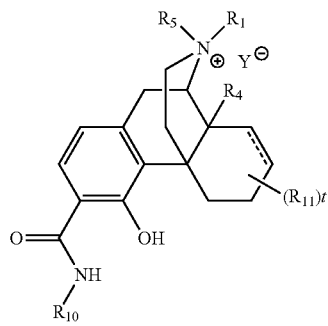

Formula VI

The invention further relates to a method of treating a disease or disorder mediated by opioid receptor comprising the step of administering a compound of Formula II or a pharmaceutically acceptable ester or prodrug thereof to a subject in need thereof.

In a more preferred embodiment, the invention relates to a compound of Formula I or II or a pharmaceutically acceptable ester or prodrug thereof, wherein $R_{10}$ is selected from Table A:

TABLE A

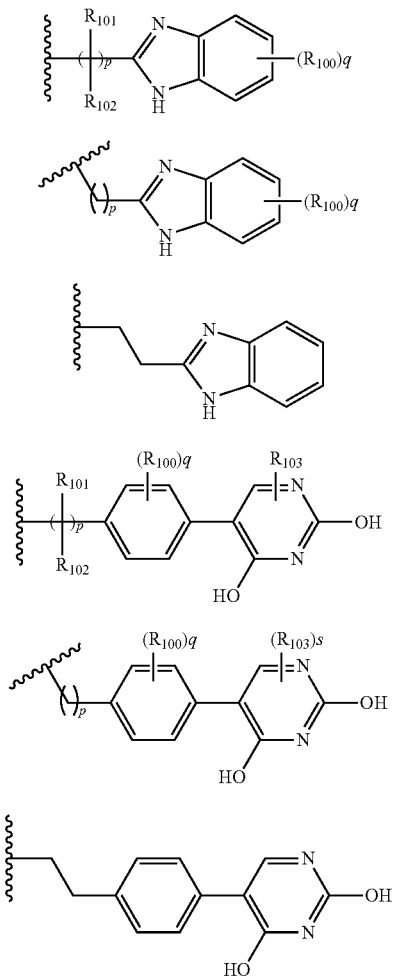

TABLE A-continued

TABLE A-continued

[Three chemical structures showing substituted pyrazole, imidazole, and imidazole variants with $(R_{100})_q$, $(R_{103})_s$, and $R_{104}$ substituents on phenyl rings]

Wherein s is 0, 1, 2, or 3;

p is 0, 1, 2, 3, 4, 5, 6, or 7;

q is 0, 1, 2, 3, 4, or 5;

Each $R_{100}$, $R_{101}$, $R_{102}$, $R_{103}$, $R_{104}$, and $R_{105}$ is independently selected from hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, optionally substituted aliphatic, optionally substituted aryl, heterocyclyl or substituted heterocyclyl.

In a preferred embodiment, the invention relates to a compound or a pharmaceutically acceptable ester or prodrug thereof, selected from Table B:

TABLE B

| No | Compound |
|----|----------|
| 1. | [Morphinan-type structure with N-cyclopropylmethyl substituent, OH, ketone, and N(R_9)(R_{10}) carboxamide] |
| 2. | [Morphinan-type structure with N-allyl substituent, OH, ketone, and N(R_9)(R_{10}) carboxamide] |

TABLE B-continued

| No | Compound |
|----|----------|
| 3. | [Morphinan-type structure with N-(3-methylbut-2-enyl) substituent, OH, ketone, and N(R_9)(R_{10}) carboxamide] |
| 4. | [Morphinan-type structure with N-cyclobutylmethyl substituent, OH, and N(R_9)(R_{10}) carboxamide] |
| 5. | [Morphinan-type structure with N-methyl substituent, OH, additional OH, double bond, and N(R_9)(R_{10}) carboxamide] |
| 6. | [Morphinan-type structure with N-methyl substituent, OH, ketone, and N(R_9)(R_{10}) carboxamide] |

TABLE B-continued

| No | Compound |
|---|---|
| 7. | |
| 8. | |
| 9. | |
| 10. | |
| 11. | |
| 12. | |
| 13. | |
| 14. | |
| 15. | |

TABLE B-continued

| No | Compound |
|----|----------|
| 16. | 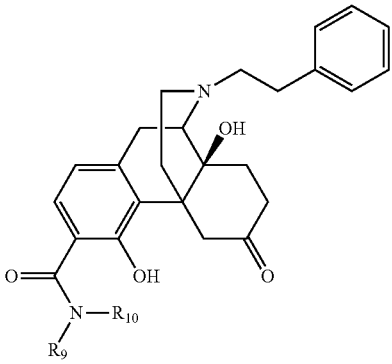 |

In a preferred embodiment, the invention relates to a compound selected from Table B, wherein $R_{10}$ is selected from Table A. In a more preferred embodiment, the invention relates to a compound selected Table B, wherein $R_{10}$ is selected from Table A and $R_9$ is hydrogen.

In a preferred embodiment, $R_1$ is selected from —$(CH_2)_a$-c-$C_3H_5$, —$(CH_2)_a$-c-$C_4H_7$, —$(CH_2)_a$—$C_5H_9$, —$(CH_2)_a$—$CH=CH_2$, —$CH_3$, —$CH_2$—$CH_2$-phenyl or —$(CH_2)_a$—$CH=C(CH_3)_2$ wherein a is independently 0, 1, 2 or 3.

In a preferred embodiment, the invention relates to a compound selected from Table C or a pharmaceutically acceptable ester or prodrug thereof:

TABLE C

| No | Compound |
|----|----------|
| 1 | 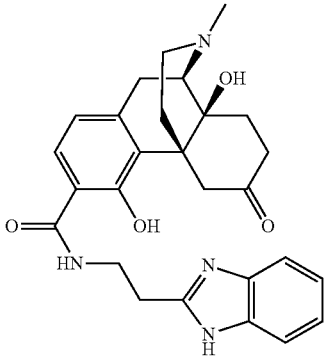 [SMILES: CN1CC[C@]23CC(=O)CC[C@@]2(O)[C@H]1Cc1ccc(C(=O)NCCc2nc4ccccc4[nH]2)c(O)c13] |
| 2 |  |
| 3 | 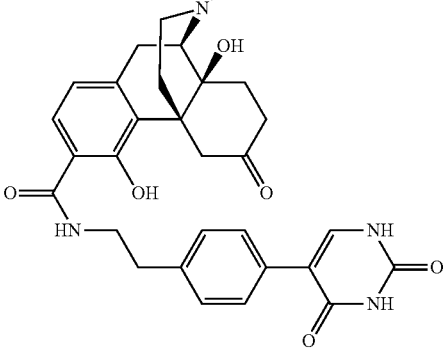 |
| 4 | 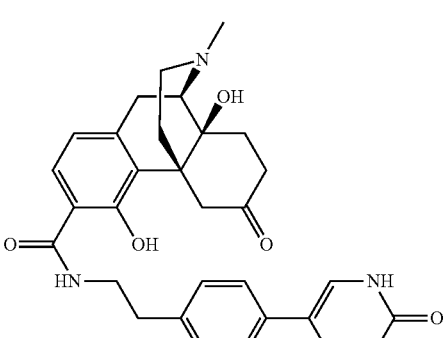 |
| 5 | 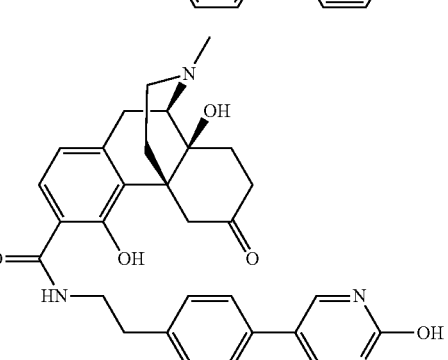 |

TABLE C-continued

| No | Compound |
|----|----------|
| 6 | |
| 7 | |
| 8 | |
| 9 | |
| 10 | |
| 11 | |
| 12 | |
| 13 | |

TABLE C-continued

| No | Compound |
|---|---|
| 14 | (structure) |
| 15 | (structure) |
| 16 | (structure) |
| 17 | (structure) |
| 18 | (structure) |

In a more preferred embodiment, the invention relates a method of treating opioid receptor mediated disease or disorder comprising the step of administering a compound of Table C to a subject in need thereof. In one embodiment, the invention relates to the treatment of pain comprising the administration of a compound of Formula I or II to a subject in need thereof. In one embodiment, the pain is selected from inflammatory pain, centrally mediated pain, peripherally mediated pain, visceral pain, structural related pain, cancer pain, soft tissue injury related pain, progressive disease related pain, neuropathic pain and acute pain from acute injury, acute pain from trauma, acute pain from surgery, chronic pain from headache, chronic pain from neuropathic conditions, chronic pain from post-stroke conditions and chronic pain from migraine. In one embodiment, the pain is associated with osteoarthritis, rheumatoid arthritis, fibromyalgia, migraine, headache, toothache, burn, sunburn, snake bite, spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulitis, causalgia, sciatic neuritis, mandibular joint neuralgia, peripheral neuritis, polyneuritis, stump pain, phantom limb pain, post-operative ileus, cholecystitis, post-mastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, cluster headache, migraine headache, peripheral neuropathy, bilateral peripheral neuropathy, diabetic neuropathy, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

In one embodiment, the invention relates to the treatment of pain associated with arthritis. In one embodiment, arthritis is selected from rheumatoid arthritis, rheumatoid spondylitis, osteoarthritis, gouty arthritis, juvenile arthritis, scapulohumeral periarthritis.

Compounds of the instant application show good binding affinities to opiate receptors. Some of the compounds of the invention show agonist activity based on their ability to induced GTPγS binding at one or more of the opiate receptors (MOR, DOR, KOR or NOP). As such, the compounds of the instant application are useful in the treatment of diseases modulated by opioid receptor activation; for example: mediating analgesia, combating drug and opioid addiction, alcohol addiction, drug overdose, mental illness, bladder dysfunctions, neurogenic bladder, interstitial cystitis, urinary incontinence, premature ejaculation, inflammatory pain, neuropathic pain, cough, lung edema, diarrhea, pruritus, cardiac disorders, cardioprotection, and cognitive, respiratory depression, irritable bowel syndrome and gastro-intestinal disorders, immunomodulation, and anti-tumor agents.

The compounds of the present invention may be used in methods to treat diseases where ligand binding primarily to the μ opioid receptor is desired. Compounds of interest may also bind to κ and δ receptors. The opioid receptors may be located in the located outside central nervous system in the periphery and located on nerve cells, immune cells, glial cells, or epithelial cells. If compounds are directly injected into the central nervous system (CNS) they would bind to opioid receptors there.

In one embodiment, the compounds are opioid receptor agonist. In another embodiment, the compounds are opioid antagonists preventing or treating a condition or disease caused by an opioid (either endogenous or exogenous). In another embodiment, compounds can function broadly in modulating opioid receptor activity having a combination of agonist and antagonist properties at the μ, κ, and δ receptors. In yet another embodiment the compounds of the invention preferably do not substantially cross the blood-brain barrier.

The compounds of the present invention may be used in methods to antagonize opioid receptors, particularly where undesirable symptoms or conditions are side effects of administering exogenous opioids. Furthermore, the compounds of the invention may be used to treat patients having disease states that are ameliorated by binding to opioid receptors or in any treatment wherein temporary suppression or modulation of the μ opioid receptor signaling is desired.

Such symptoms, conditions or diseases include the complete or partial antagonism of opioid-induced sedation, confusion, respiratory depression, euphoria, dysphoria, hallucinations, pruritus (itching), increased biliary tone, increased biliary colic, and urinary retention, ileus, emesis, and addiction liability; prevention or treatment of opioid and cocaine dependence; rapid opioid detoxification; treatment of alcoholism; treatment of alcoholic coma; detection of opioid use or abuse (pupil test); treatment of eating disorders; treatment of obesity; treatment of post-concussional syndrome; adjunctive therapy in septic, hypovolemic or endotoxin-induced shock; potentiation of opioid analgesia (especially at ultra-low doses); reversal or prevention of opioid tolerance and physical dependence (especially at ultra-low doses); prevention of sudden infant death syndrome); treatment of dyskinesia; treatment of metabolic diseases, including Type 1 and 2 diabetes; treatment of the endocrine system (including increased release of luteinizing hormone, treatment of infertility, increasing number of multiple births in animal husbandry, and male and female sexual behavior); treatment of the immune system and cancers associated with binding of the opioid receptors; treatment of anxiolysis; treatment of diuresis; treatment and regulation of blood pressure; treatment of tinnitus or impaired hearing; treatment of epilepsy; treatment of cachexia; treatment of general cognitive dysfunctions; and treatment of kleptomania.

The compounds of the present invention may also be used as cytostatic agents, as antimigraine agents, as immunomodulators, as immunosuppressives, as antiarthritic agents, as antiallergic agents, as virucides, to treat diarrhea, as antischizophrenics, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present compounds may be used in the treatment of Parkinson's disease as an adjunct to L-dopa for treatment dyskinesia associated with the L-dopa treatment.

In certain embodiments, the compounds of the invention may be used in methods for preventing or treating gastrointestinal dysfunction, including, but not limited to, irritable bowel syndrome, opioid-bowel dysfunction, colitis, post-operative and opioid-induced emesis (nausea and vomiting), decreased gastric motility and emptying, inhibition of small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, and delayed absorption of orally administered medications or nutritive substances.

In one embodiment, the compositions of the invention may further comprise one or more compounds that may be designed to enhance the analgesic potency of the opioid and/or to reduce analgesic tolerance development. Such compounds include, for example, dextromethorphan or other NMDA antagonists (Mao, M. J. et al., Pain, 1996, 67, 361), L-364,718 and other CCK antagonists (Dourish, C. T. et al., Eur. J. Pharmacol., 1988, 147, 469), NOS inhibitors (Bhargava, H. N. et al., *Neuropeptides,* 1996, 30, 219), PKC inhibitors (Bilsky, E. J. et al., *J. Pharmacol. Exp. Ther.,* 1996, 277, 484), and dynorphin antagonists or antisera (Nichols, M. L. et al., *Pain,* 1997, 69, 317). The disclosures of each of the foregoing documents are hereby incorporated herein by reference, in their entireties.

In one embodiment, the compounds of the invention can be used in methods for preventing or treating post-operative or opioid-induced ileus. In another embodiment, the compounds of the invention can be used as an analgesics, anesthetics, anti-pruritics, anti-diarrheal agents, anti-convulsants, anti-tussives, and/or anorexics.

DEFINITIONS

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted.

In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "compound" "drug", and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount" with respect to the subject method of treatment, refers to an amount of the subject compound which, when delivered as part of desired dose regimen, brings about management of the disease or disorder to clinically acceptable standards.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, hetoerarylalkylene and heterocycloalkylene groups are to be included in the above definitions, and are applicable to provide the formulas herein with proper valency.

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described herein, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion. Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc., delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis,* 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2- trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from the injection site. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide or polylactide-co-glycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

In one embodiment, administration of the microparticles comprising iloprost or another pharmaceutical agent to be administered in addition to iloprost provides local or plasma concentrations sustained at approximately constant values over the intended period of release (e.g., up to 2 to 24 hours, to enable dosing once, twice, three times, four times or more than four times per day). The microparticle formulations may allow patients to take treatments less frequently, and to receive more prolonged and steadier relief.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluents such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The total daily dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 1 mg to about 200 mg of the compound(s) of this invention per day or per weekly or per bi-weekly in single or multiple doses.

Dosing schedules may be adjusted to provide the optimal therapeutic response. For example, administration can be one to three times daily for a time course of one day to several days, weeks, months, and even years, and may even be for the life of the patient. Practically speaking, a unit dose of any given composition of the invention or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Unless otherwise defined, all technical and scientific terms used herein are accorded the meaning commonly known to one with ordinary skill in the art.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

The morphinan compounds according to the present invention may be synthesized employing methods taught, for example, in U.S. Pat. Nos. 5,250,542, 5,434,171, 5,159,081, and 5,270,328. The optically active and commercially available naltrexone that can be employed as starting material in the synthesis of some of the compounds of the invention may be prepared by the general procedure taught in U.S. Pat. No. 3,332,950.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Synthesis of Heterocyclic Bi-Aryls

Example 1

Synthesis of tert-butyl 4-bromophenethylcarbamate

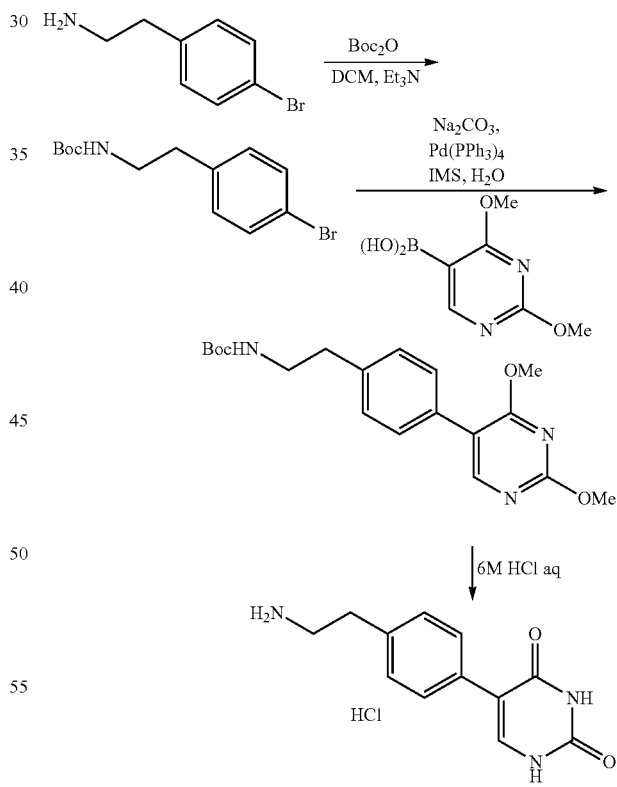

Bromophenethylamine (50 g, 250 mmol) and triethylamine (105 mL, 750 mmol) were stirred in dichloromethane (DCM; 1.5 L), and cooled to 0° C. Boc anhydride (82 g, 375 mmol) was added and the reaction mixture stirred at room temperature overnight. The reaction mixture was washed with water (1 L), brine (500 mL), dried (MgSO$_4$) and concentrated to give an orange oil. The crude residue was crystallized from hexane (250 mL) to give a white solid, tert-butyl 4-bromophenethylcarbamate (39.85 g, 133 mmol, 53%).

Example 2

Synthesis of tert-butyl 4-(2,4-dimethoxypyrimidin-5-yl)phenethylcarbamate

Industrial methylated spirits (IMS; 15 mL) and water (5 mL) were degassed thoroughly. tert-butyl 4-bromophenethylcarbamate (1.08 g, 3.63 mmol), sodium carbonate (1.54 g, 14.52 mmol), palladium tetrakis (0.42 g, 0.36 mmol) and 2,4-dimethoxy-5-pyrimidinylboronic acid (1.00 g, 5.44 mmol) were added and the reaction mixture heated to 90° C. for 18 hours. No starting material was observed by LCMS. Water (100 ml) and ethyl acetate (300 ml) were added and the organic layer separated. The organic layer was washed with water (100 ml), dried (MgSO$_4$) and concentrated to give a yellow oil. The crude residue was subject to column chromatography (20 to 60% ethyl acetate/hexane) to give a yellow oil, tert-butyl 4-(2,4-dimethoxypyrimidin-5-yl)phenethylcarbamate, which crystallized on standing (1.18 g, 3.28 mmol, 91%).

Example 3

Synthesis of 5-(4-(2-aminoethyl)phenyl)pyrimidine-2,4(1H,3H)-dione hydrochloride To tert-butyl 4-(2,4-dimethoxypyrimidin-5-yl)phenethylcarbamate (0.5 g, 1.39 mmol) was added aqueous hydrochloric acid (6 M, 15 mL) and the reaction mixture stirred at reflux for 4 hours. No starting material was observed by LCMS. The precipitate was filtered, washed with water (5 mL) and dried under reduced pressure (50° C.) to give a pale yellow solid, 5-(4-(2-aminoethyl)phenyl)pyrimidine-2,4(1H,3H)-dione hydrochloride (0.32 g, 1.35 mmol, 86%).

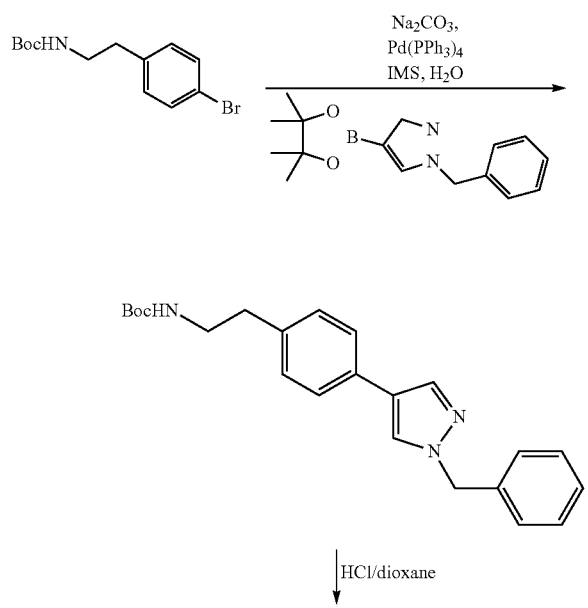

Example 4

Synthesis of tert-Butyl 4-(6-oxo-1,6-dihydropyridin-3-yl)phenethylcarbamate

IMS (50 mL) and water (16 mL) were degassed thoroughly. tert-Butyl 4-bromophenethylcarbamate (3.52 g, 11.7 mmol), sodium carbonate (5.0 g, 46.9 mmol), palladium tetrakis (1.35 g, 1.2 mmol) and 1-benzyl-1H-pyrazole-4-boronic acid pinacol ester (5.0 g, 17.6 mmol) were added and the reaction mixture heated to 90° C. overnight. The reaction was partitioned between ethyl acetate (500 mL) and water (250 mL) and brine (250 mL), then dried (MgSO$_4$). Filtration and removal of the solvent gave the crude residue which was subject to column chromatography (50% ethyl acetate/heptane) to give tert-butyl 4-(6-oxo-1,6-dihydropyridin-3-yl) phenethylcarbamate (4.2 g, 11.1 mmol, 95% yield).

Example 5

Synthesis of 2-(4-(1-Benzyl-1H-pyrazol-4-yl)phenyl)ethanamine hydrochloride

To tert-butyl 4-(6-oxo-1,6-dihydropyridin-3-yl)phenethylcarbamate (4.2 g, 11.1 mmol) was added HCl/dioxane (approximately 4 M, 100 mL). After 5 minutes, the reaction mixture had stopped stirring and a further 50 mL HCl/dioxane was added. The reaction was stirred at room temperature for 6 hours. The solvent was removed under reduced pressure giving 2-(4-(1-benzyl-1H-pyrazol-4-yl)phenyl)ethanamine hydrochloride as a yellow solid (4.0 g, 11.1 mmol, 100% yield).

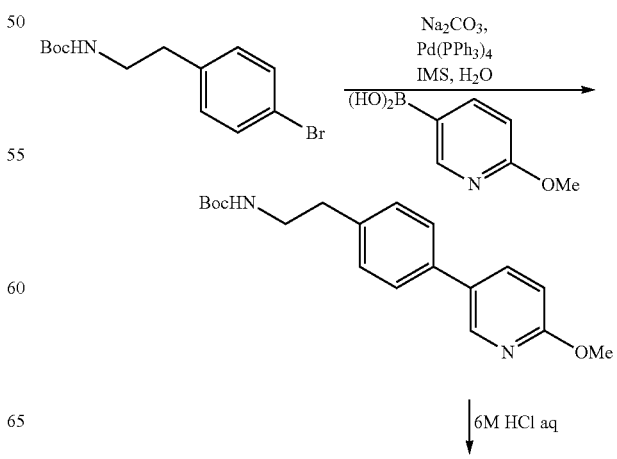

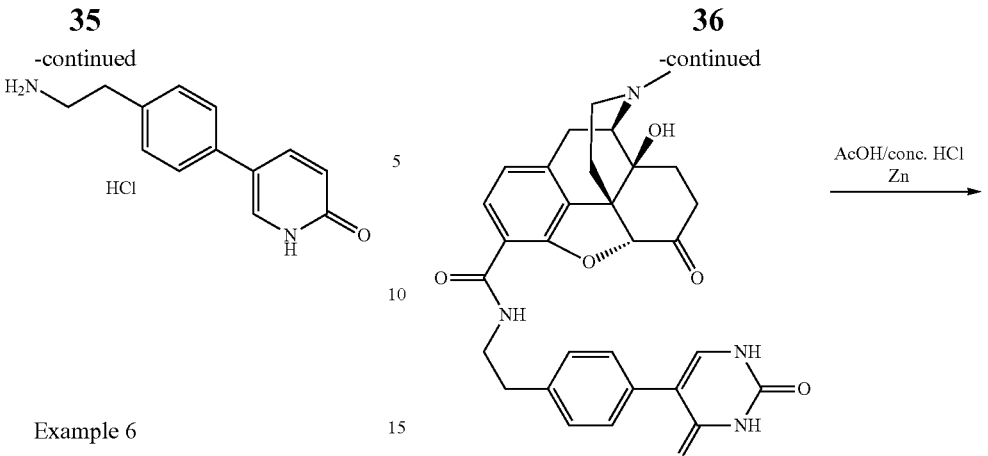

Example 6

Synthesis of tert-Butyl 4-(6-oxo-1,6-dihydropyridin-3-yl)phenethylcarbamate

IMS (600 mL) and water (250 mL) were degassed thoroughly. tert-Butyl 4-bromophenethylcarbamate (32.7 g, 109 mmol), sodium carbonate (46.2 g, 436 mmol), palladium tetrakis (12.6 g, 11.0 mmol) and 2-methoxypyridine boronoic acid (25.0 g, 163 mmol) were added and the reaction mixture heated to 90° C. for 18 hours. The reaction was cooled to room temperature, filtered and the residue washed with IMS (100 mL) and ethyl acetate (1 L). The filtrate was washed with water (500 mL), dried (MgSO₄) and concentrated to give a brown solid. The crude residue was subject to column chromatography (0 to 1.5% MeOH in DCM) to give a white solid, tert-butyl 4-(6-oxo-1,6-dihydropyridin-3-yl)phenethylcarbamate (20.95 g, 63.8 mmol, 58% yield).

Example 7

Synthesis of 5-(4-(2-Aminoethyl)phenyl)pyridin-2(1H)-one hydrochloride

To tert-butyl 4-(6-oxo-1,6-dihydropyridin-3-yl)phenethylcarbamate (10.25 g, 31.0 mmol) was added aqueous hydrochloric acid (6 M, 220 mL) and the reaction mixture stirred at reflux overnight. The reaction was cooled to room temperature and the precipitate was filtered, washed with water (5 mL) and dried under reduced pressure (50° C.). The acidic solution was concentrated under reduced pressure and the resultant solid combined with the filtered solid to give 5-(4-(2-aminoethyl)phenyl)pyridin-2(1H)-one hydrochloride (7.80 g, 31.0 mmol, 100% yield).

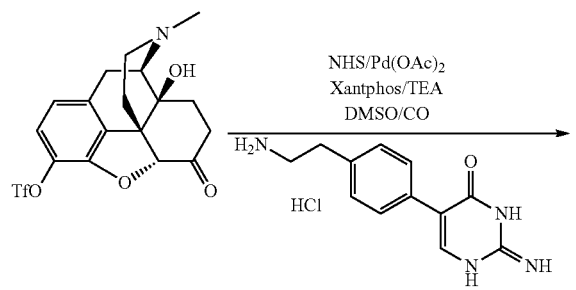

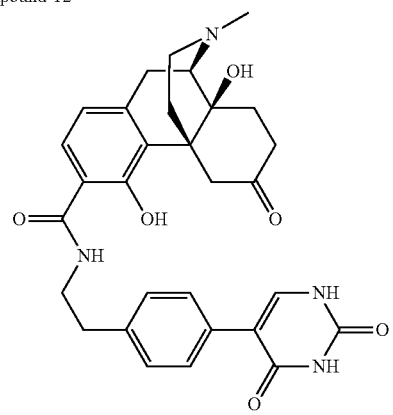

Compound-12

Synthesis of Opioids

Example 8

Synthesis of Compound 4

To a solution of the crude Compound 12 (52 g) in acetic acid (1 L) at 90° C. was added concentrated HCl (35 mL). To this was then added zinc powder (64 g, 0.98 mol) over 35 minutes and after complete addition a further portion of concentrated HCl (40 mL) was added over 5 minutes. To the reaction mixture was then added a second portion of zinc powder (64 g, 0.98 mol) over 1 hour. After 30 minutes a third portion of zinc powder (32 g, 0.49 mol) and the reaction heated a further 1 hour. The reaction was cooled to ~60° C. and filtered and the zinc residue washed with warm acetic acid. The filtrate was concentrated under reduced pressure and the residue diluted with concentrated ammonia (1 L) and 2-methyltetrahydrofuran (1 L) and waster (0.5 L). The mixture was stirred for 10 minutes and the liquids decanted from the brown gum. The gum was washed with water and all the liquid combined. The organic phase was separated, dried over MgSO₄ and combined with the brown gum and concentrated under reduced pressure. The resulting residue was dissolved in dichloromethane/methanol (8:2) and columned on a short plug of silica eluting with dichloromethane/methanol (8:2) and then dichloromethane/methanol/triethylamine (16:3:1). The product containing fractions were evaporated and re-columned eluting with dichloromethane/methanol (9:1) and then dichloromethane/(16% NH₃/methanol) (9:1). The product obtained from this was then further purified by prep. HPLC to give Compound 4; LC/MS 545 (M+H)+; NMR (DMSO-D$_6$): 1.30-2.10 (6H, m), 2.12-3.05 (11H, m), 3.10-3.60 (2H, m), 4.04 (1H, bs), 4.58 (1H, s), 6.42 (1H, bs), 7.19 (2H, d), 7.40-7.60 (5H, m), 10.45 (3H, bs).

Example 9

Synthesis of Compounds 13 and 14

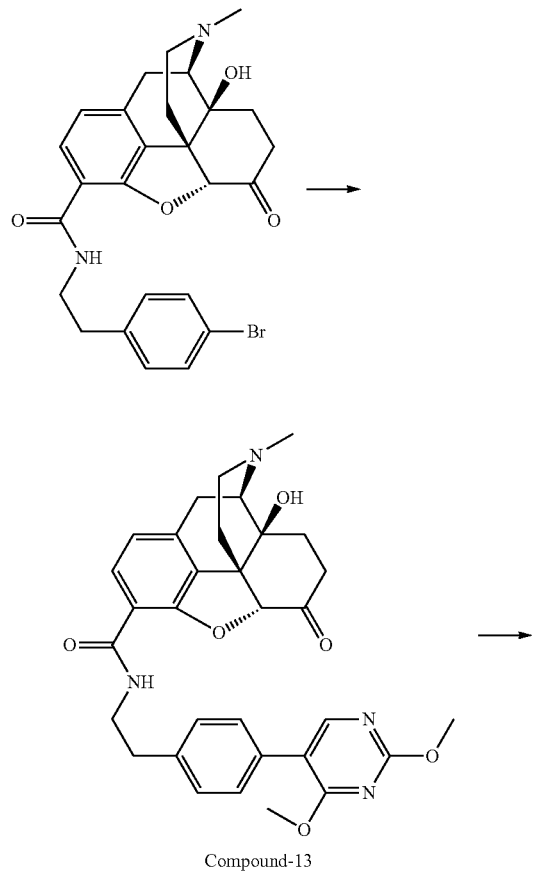

Compound-13

Compound-14

A solution of (5a)-N-[2-(4-bromophenyl)ethyl]-14-hydroxy-17-methyl-6-oxo-4,5-epoxymorphinan-3-carboxamide (1.7 g, 3.3 mmol) in denatured ethanol (15 mL) was degassed with argon for 20 min and then Na$_2$CO$_3$ (1.4 g, 13.3 mmol), 2,4-dimethoxypyrimidin-5-ylboronic acid (0.92 g, 5.0 mmol), degassed water (5 mL) and Pd(PPh$_3$)$_4$ (0.38 g, 0.33 mmol) added. The reaction was sealed and heated in a microwave reactor at 120° C. for 25 min. The reaction was concentrated to ~10 mL, diluted with dichloromethane (50 mL) and washed with water (40 mL). The organic phase was dried over MgSO$_4$, filtered and evaporated. The residue was further purified on silica eluting with dichloromethane to methanol/dichloromethane (1:9). The product containing fraction were re-purified on silica eluting with dichloromethane/ethyl acetate (9:1) to dichloromethane/ethyl acetate/methanol (8:1:1) to give the Compound 13 (1.38 g, 73%) as a yellow oil.

To a mixture of Compound 13 (0.70 g, 1.2 mmol) and sodium iodide (1.33 g, 4.9 mmol) in anhydrous acetonitrile (8 mL) was added chlorotrimethylsilane (0.63 mL, 4.9 mmol) and the reaction mixture stirred for 5 h. The reaction mixture was diluted with 5% aqueous sodium sulfite (5 mL) and water (10 mL) and then made basic with saturated aqueous sodium carbonate. This was extracted with twice with dichloromethane (80 mL) and once with ethyl acetate (50 mL). The organic layers were combined and evaporated to give a yellow solid. This was partially dissolved in 2M HCl and the insoluble material was filtered off with celite. The aqueous phase was made basic with saturated sodium carbonate and the resulting white solid filtered and dried under vacuum. This was then purified on silica eluting with dichloromethane/methanol (9:1) to give Compound 14 (197 mg). Compound 14 was dissolved in dichloromethane (5 mL) and 4M HCl in diethyl ether (40 mL) added. The mixture was stirred for 2.5 h and evaporated to give the chloride salt of Compound 14 ((0.21 g, 29%) as a white solid; LC/MS 543 (M+H)+;

NMR (DMSO-D$_6$): 1.40-1.57 (2H, m), 1.90-2.01 (1H, m), 2.10-2.20 (1H, m), 2.58-2.70 (1H, m), 2.75-2.92 (5H, m), 2.92-3.15 (3H, m), 3.30-3.65 (4H, m), 5.31 (1H, s), 6.79 (1H, s), 6.93 (1H, d), 7.26 (2H, d), 7.44 (2H, d), 7.55 (1H, d), 7.60-7.70 (2H, m), 9.36 (1H, bs), 11.10 (1H, bs), 11.20 (1H, bs).

Example 10

Synthesis of Compound 10

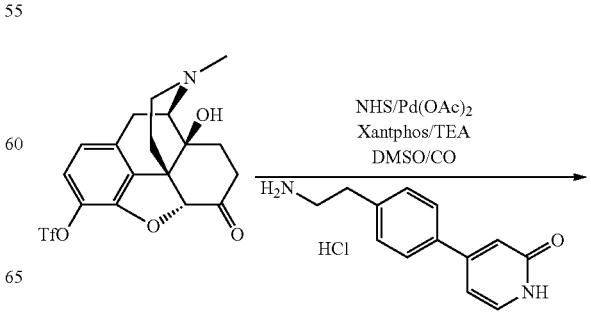

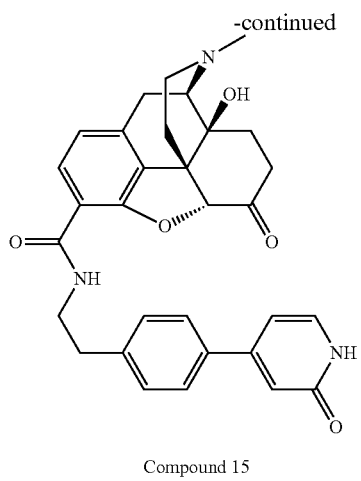

Compound 15

AcOH/conc. HCl
Zn

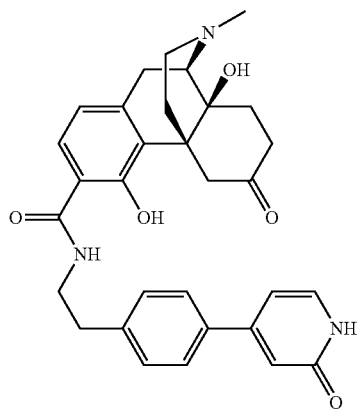

Compound 10

Oxymorphone triflate (3.0 g, 7.0 mmol) was stirred in degassed DMSO (40 mL). N-hydroxysuccinimide (1.60 g, 13.9 mmol) was added followed by triethylamine (1.94 mL, 13.9 mmol), palladium acetate (156 mg, 0.7 mmol) and xantphos (402 mg, 0.7 mmol). The reaction mixture was stirred at 70° C. under an atmosphere of CO overnight. Further palladium acetate (1.04 g, 4.61 mmol) and xantphos (2.68 g, 4.63 mmol) were added and the reaction mixture heated 6 hours 70° C. under an atmosphere of CO. The mixture was allowed to return to room temperature before the addition of 4-(4-(2-aminoethyl)phenyl)pyridin-2(1H)-one hydrochloride (2.0 g, 8.0 mmol) and triethylamine (2 mL, 14.3 mmol). The reaction was stirred for 1 hour before removal of the DMSO under reduced pressure. The residue was subject to column chromatography (0 to 5% MeOH($NH_3$) in DCM). The isolated residue was found to still contain DMSO and was portioned between DCM (500 mL) and water (250 mL). The aqueous phase was extracted a further five times until the product was completely extracted. The organic phases were combined and the solvent removed under reduced pressure giving (4R,4aS,7aR,12bS)-4a-hydroxy-3-methyl-7-oxo-N-(4-(2-oxo-1,2-dihydropyridin-4-yl)phenethyl)-2,3,4,4a,5,6,7,7a-octahydro-1H-4,12-methanobenzofuro[3,2-e]isoquinoline-9-carboxamide (Compound 15; 1.2 g, 2.3 mmol, 33% yield).

To a solution of the crude Compound 15 (52 g) in acetic acid (55 mL) was added zinc powder (3.03 g, 45.8 mmol) followed by concentrated $HCl_{(aq)}$ (2 mL). The reaction was heated at 90° C. for 2 hours. The reaction mixture was allowed to cool to 60° C. and filtered. The zinc residue was washed with further acetic acid (30 mL). The combined acetic acid solutions were concentrated under reduced pressure. The residue was basified with ammonium hydroxide solution (28%) and extracted with Me-THF (2×250 mL). The organic phase was dried ($MgSO_4$), filtered, and the solvent removed under reduced pressure. The crude product was subject to column chromatography (0 to 5% MeOH($NH_3$) in DCM) followed by prep-HPLC to give Compound 10 (4,14-dihydroxy-N-{2-[4-(2-hydroxypyridin-4-yl)phenyl]ethyl}-17-methyl-6-oxomorphinan-3-carboxamide) (378 mg, 0.72 mmol, 31% yield) as a white solid; LC/MS 528 (M+H)$^+$; NMR (DMSO-$D_6$): 533-20-7__1H-3.jdf: 1.45 (1H, d), 1.58-2.10 (4H), 1.8 (3H, s), 2.19-2.38 (1H, m), 2.40-3.10 (10H, m), 3.78 (1H, d), 4.68 (1H, bs), 6.46 (1H, dd), 6.53 (1H, s), 6.61 (1H, d), 7.31 (2H, d), 7.39 (1H, d), 7.53 (1H, d), 7.60 (2H, d), 8.96 (1H, bs).

Example 11

Synthesis of Compound 7

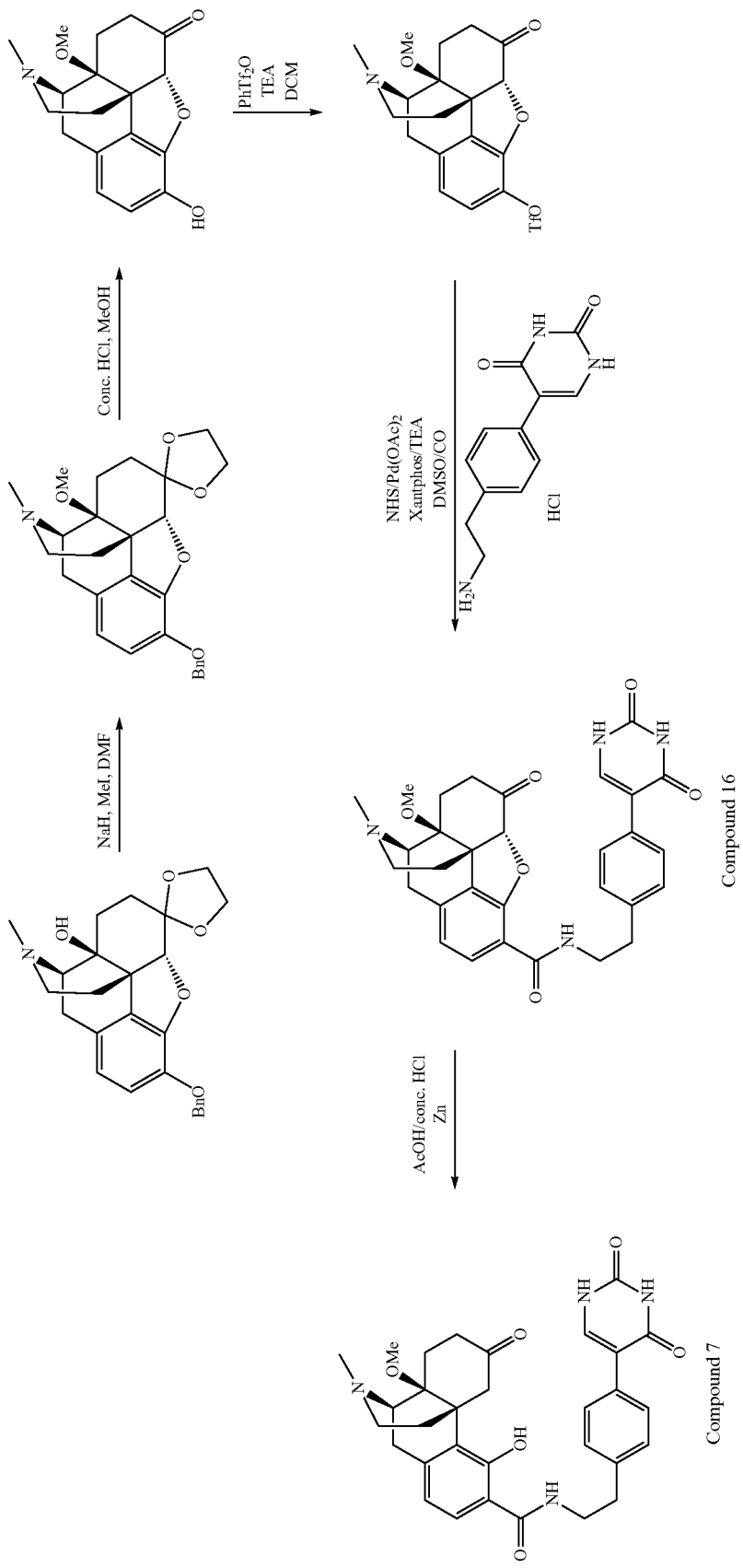

To an ice cold solution of (4a'S,7a'R)-9'-(benzyloxy)-3'-methyl-1',2',3',4',5',6'-hexahydro-4a'H-spiro[1,3-dioxolane-2,7'-[4,12]methano[1]benzofuro[3,2-e]isoquinolin]-4a'-ol (10 g, 23 mmol) in DMF (100 mL) was added portionwise sodium hydride (4.6 g, 115 mmol). The mixture was stirred cold for 2 hours then methyl iodide (2.9 mL, 45.9 mmol) was added in one portion. The reaction was warmed to room temperature and stirred overnight. The mixture was poured into water (500 mL) and extracted into DCM (2×500 mL). The organic layer was washed with water (3×300 mL) and brine (300 mL), dried (MgSO₄), filtered and concentrated to give the crude product. The product was purified by silica column chromatography (eluting 0-10% ammonia/methanol in DCM) to give the product (4R,4aS,7aR,12bS)-9-(benzyloxy)-4a-methoxy-3-methyl-1,2,3,4,4a,5,6,7a-octahydrospiro[4,12-methanobenzofuro[3,2-e]isoquinoline-7,2'-[1,3]dioxolane] as a viscous yellow oil (7.3 g, 71% yield).

To a solution of (4R,4aS,7aR,12bS)-9-(benzyloxy)-4a-methoxy-3-methyl-1,2,3,4,4a,5,6,7a-octahydrospiro[4,12-methanobenzofuro[3,2-e]isoquinoline-7,2'-[1,3]dioxolane] (7.3 g, 16.2 mmol) in MeOH (75 mL) was added conc. HCl (50 mL). The mixture was refluxed for 5 hours then cooled with an ice bath. Concentrated ammonia (25%) was added until pH 8 was reached. The mixture was concentrated and the residues stirred with 10% MeOH/DCM (1 L) overnight. The mixture was filtered and the liquors concentrated to give (4R,4aS,7aR,12bS)-9-hydroxy-4a-methoxy-3-methyl-2,3,4,4a,5,6-hexahydro-1H-4,12-methanobenzofuro[3,2-e]isoquinolin-7(7aH)-oneas a dark red oil (5.3 g, quantitative yields).

A mixture of (4R,4aS,7aR,12bS)-9-hydroxy-4a-methoxy-3-methyl-2,3,4,4a,5,6-hexahydro-1H-4,12-methanobenzofuro[3,2-e]isoquinolin-7(7aH)-one (5.1 g, 16.2 mmol), N-Phenylbis(trifluoromethanesulfonamide) (6 g, 16.7 mmol), triethylamine (6.8 mL, 48.5 mmol) and DCM (80 mL) was stirred at room temperature overnight. The mixture was concentrated under reduced pressure to give the crude product still containing triflating reagent. This was dissolved in 4:1 mixture of ethyl acetate/hexane (200 mL) and washed with water (5×150 mL). The organic layer was dried (MgSO₄), filtered and concentrated under reduced pressure to give the product (4R,4aS,7aR,12bS)-4a-methoxy-3-methyl-7-oxo-2,3,4,4a,5,6,7,7a-octahydro-1H-4,12-methanobenzofuro[3,2-e]isoquinolin-9-yl trifluoromethanesulfonate as a brown oil (5.9 g, 81% yield). Compounds 7 and 16 were synthesized from the above intermediate in a similar procedure as in the synthesis of compounds 10 and 15.

Example 12

Synthesis of Compound 11

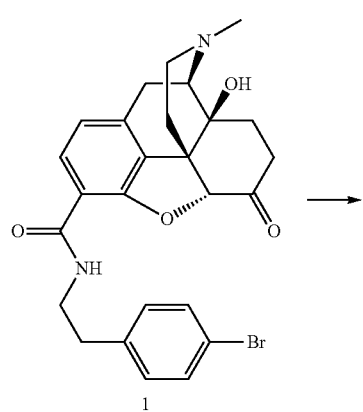

1

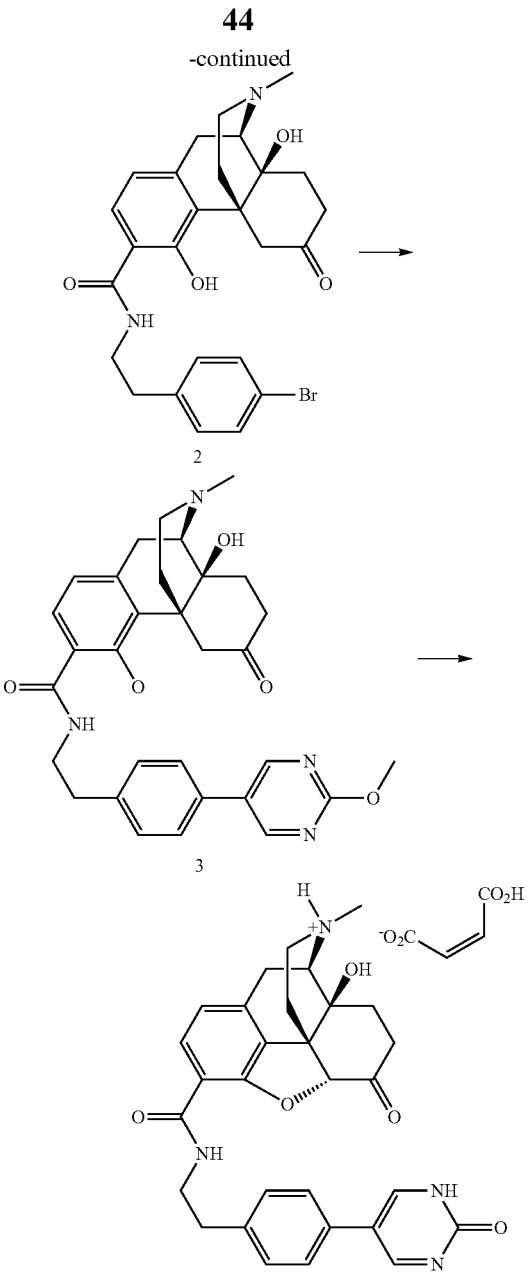

Compound 11

A mixture of (5a)-N-[2-(4-bromophenyl)ethyl]-14-hydroxy-17-methyl-6-oxo-4,5-epoxymorphinan-3-carboxamide (1) (10 g, 19.6 mmol), denatured ethanol (300 mL), zinc powder (28 g, 0.43 mol) and ammonium chloride (34.5 g, 0.65 mol) was heated at reflux for 30 min and then cooled to ~40° C. The reaction mixture was filtered through celite and washed with denatured ethanol (300 mL, 40° C.). The volatiles were removed under vacuum and the residue partitioned between dichloromethane (200 mL) and 2% aqueous ammonia (300 mL). The aqueous phase was further extracted with dichloromethane (2×200 mL) and the combined organics were dried over MgSO₄ and evaporated. The residue was purified on silica eluting with dichloromethane/methanol (95:5 to 9:1) to give N-[2-(4-bromophenyl)ethyl]-4,14-dihydroxy-17-methyl-6-oxomorphinan-3-carboxamide (2) (7.95 g, 79%) as a brown solid.

To a degassed mixture of ethanol and water (4:1, 20 mL) was added 2-methoxypyrimidin-5-ylboronic acid (0.67 g, 4.4 mmol), Na₂CO₃ (1.24 g, 11.7 mmol) and N-[2-(4-bromophenyl)ethyl]-4,14-dihydroxy-17-methyl-6-oxomorphinan-3-carboxamide (2) (1.5 g, 2.9 mmol). The reaction mixture was further degassed and then Pd(PPh₃)₄ (0.32 g, 0.3 mmol) added. The reaction mixture was heated in a microwave reactor at 120° C. for 25 min. and cooled. The reaction mixture was diluted with ethyl acetate (50 mL) and washed with 1:1 brine/water (3×35 mL). The organic phase was dried over MgSO₄, filtered and evaporated. The resulting residue was further purified on silica eluting with dichloromethane/methanol (9:1) to give 4,14-dihydroxy-N-{2-[4-(2-methoxypyrimidin-5-yl)phenyl]ethyl}-17-methyl-6-oxomorphinan-3-carboxamide (3) (0.50 g, 32%) as a yellow foam.

A mixture of 4,14-dihydroxy-N-{2-[4-(2-methoxypyrimidin-5-yl)phenyl]ethyl}-17-methyl-6-oxomorphinan-3-carboxamide (3) (0.5 g, 0.9 mmol) and pyridine hydrochloride (5 mL) was heated at 150° C. for 6 h. The reaction mixture was cooled, basified with saturated aqueous sodium bicarbonate and extracted with dichloromethane (3×40 mL). The aqueous phase was filtered and the collected brown solid was combined with the organic washes and evaporated to dryness. The residue was purified on silica eluting with dichloromethane/methanol (9:1) to dichloromethane/16% NH₃ in methanol (9:1) to give 4,14-dihydroxy-17-methyl-6-oxo-N-{2-[4-(2-oxo-1,2-dihydropyrimidin-5-yl)pheyl]ethyl}morphinan-3-carboxamide (RDC6139) (0.15 g) as a white solid. This was dissolved in dichloromethane/methanol (3:1, 20 mL) and maleic acid (32 mg, 1 eq) added. The reaction mixture was stirred for 4 h and then the volatiles removed under vacuum at 40° C. The residue was freeze dried from water to give Compound 11 4,14-dihydroxy-17-methyl-6-oxo-N-{2-[4-(2-oxo-1,2-dihydropyrimidin-5-yl)phenyl]ethyl}morphinan-3-carboxamide maleate salt (0.17 g, 98%) as a white solid; LC/MS 529 (M+H)⁺; NMR (D₂O): 1.15-1.21 (4H, m), 1.49-1.60 (1H, m), 1.65-1.90 (3H, m), 2.10-2.22 (1H, m), 2.29-2.41 (1H, m), 2.50-2.72 (5H, m), 2.90-3.00 (1H, m), 3.18-3.40 (3H, m), 3.45-3.60 (2H, m), 6.04 (2H, s), 6.95-7.05 (4H, m), 7.26 (1H, m), 8.11 (2H, bs).

Example 13

Synthesis of Compound 5

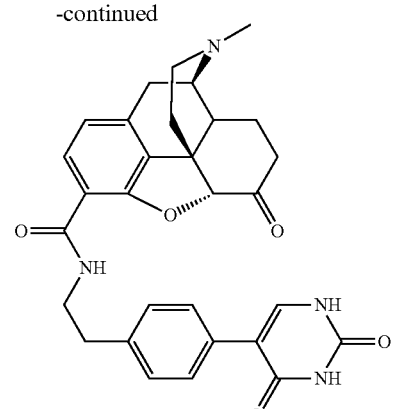

Compound 17

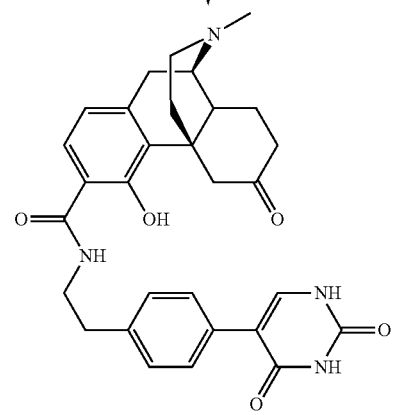

Compound 5

A mixture of Hydromorphone HCl (100 g, 0.31 mol), N-Phenylbis(trifluoromethanesulfonamide) (114 g, 0.32 mol), diisopropylethylamine (215 mL, 1.24 mol) and DCM (2 L) was stirred at room temperature overnight. The mixture was concentrated under reduced pressure to give the crude product still containing triflating reagent. This was dissolved in 4:1 mixture of ethyl acetate/hexane (1 L) and washed with water (6×1 L). The organic layer was dried (MgSO₄), filtered and concentrated under reduced pressure to give the product (4R,7aR,12bS)-3-methyl-7-oxo-2,3,4,4a,5,6,7,7a-octahydro-1H-4,12-methanobenzofuro[3,2-e]isoquinolin-9-yl trifluoromethanesulfonate as a white solid (120 g, 93% yield) (4R,7aR,12bS)-3-methyl-7-oxo-2,3,4,4a,5,6,7,7a-octahydro-1H-4,12-methanobenzofuro[3,2-e]isoquinolin-9-yl trifluoromethanesulfonate (5 g, 11.98 mmol) was stirred in degassed DMSO (80 mL). N-hydroxysuccinimide (2.76 g, 23.96 mmol) was added followed by triethylamine (3.3 mL, 23.96 mmol), palladium acetate (0.27 g, 1.2 mmol) and xantphos (0.69 g, 1.2 mmol). The reaction mixture was stirred at 70° C. under an atmosphere of CO overnight. The mixture was allowed to return to room temperature before the addition of 5-(4-(2-aminoethyl)phenyl)pyrimidine-2,4(1H,3H)-dione hydrochloride (3.2 g, 11.98 mmol) and triethylamine (3.3 mL, 23.96 mmol). The reaction was stirred for 5 hours before

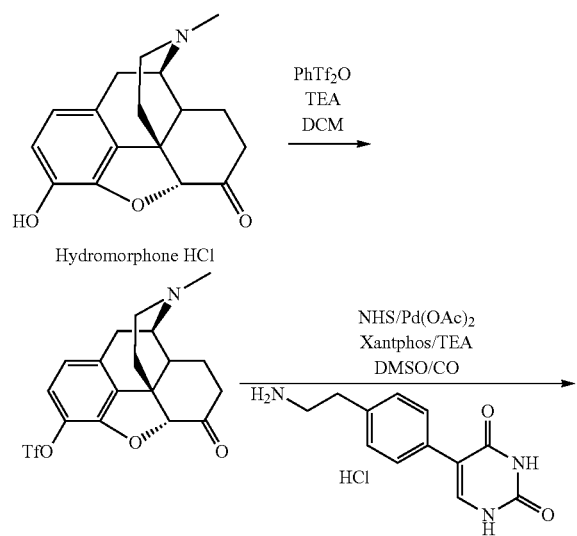

removal of the DMSO under reduced pressure. The residue was stirred with DCM and filtered to give a brown solid, which was used as it was for the next step (4R,7aR,12bS)—N-(4-(2,4-dioxo-1,2,3,4-tetrahydropyrimidin-5-yl)phenethyl)-3-methyl-7-oxo-2,3,4,4a,5,6,7,7a-octahydro-1H-4,12-methanobenzofuro[3,2-e]isoquinoline-9-carboxamide (6 g, 79% crude yield).

To a solution of the crude (4R,7aR,12bS)—N-(4-(2,4-dioxo-1,2,3,4-tetrahydropyrimidin-5-yl)phenethyl)-3-methyl-7-oxo-2,3,4,4a,5,6,7,7a-octahydro-1H-4,12-methanobenzofuro[3,2-e]isoquinoline-9-carboxamide (5 g) in acetic acid (200 mL) was added zinc powder (12.6 g, 190 mmol) followed by concentrated $HCl_{(aq)}$ (7.5 mL). The reaction was heated at 90° C. for 2.5 hours. Further zinc powder (47.6 g, 717 mmol) was added portionwise over 24 hours. After cooling to room temperature, the zinc salts were removed by filtration and washed with further acetic acid (80 mL). The combined acetic acid solutions were concentrated under reduced pressure. The residue was basified with ammonium hydroxide solution (28%) and extracted with Me-THF (3×500 mL). The organic phase was dried ($MgSO_4$), filtered, and the solvent removed under reduced pressure. The crude product purified by prep-HPLC to give Compound 5 (4bS, 9R)—N-(4-(2,4-dioxo-1,2,3,4-tetrahydropyrimidin-5-yl)phenethyl)-4-hydroxy-11-methyl-6-oxo-6,7,8,8a,9,10-hexahydro-5H-9,4b-(epiminoethano)phenanthrene-3-carboxamide as a white solid (0.89 g, 18% yield); LC/MS 529 $(M+H)^+$; NMR (DMSO-$D_6$): 1.25-1.50 (1H, m), 1.55-1.89 (4H, m), 1.98 (1H, d), 2.05-3.00 (7H, m), 3.20-3.60 (6H, m), 4.01 (1H, d), 6.61 (1H, d), 7.19 (2H, d), 7.45 (2H, d), 7.50-7.64 (4H, m), 8.90 (1H, bs), 11.20 (1H, bs), 13.86 (1H, bs).

Example 14

Synthesis of Compound 2

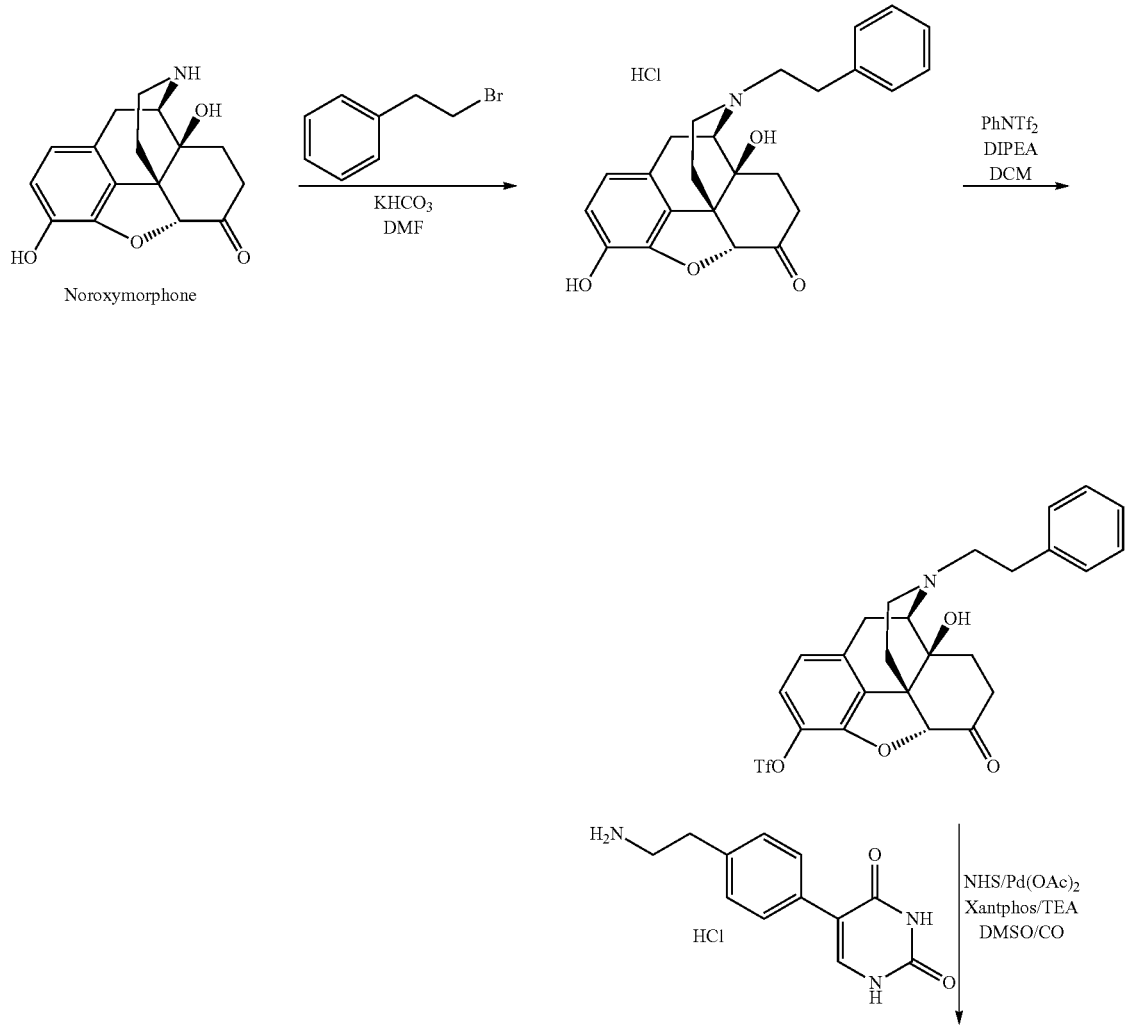

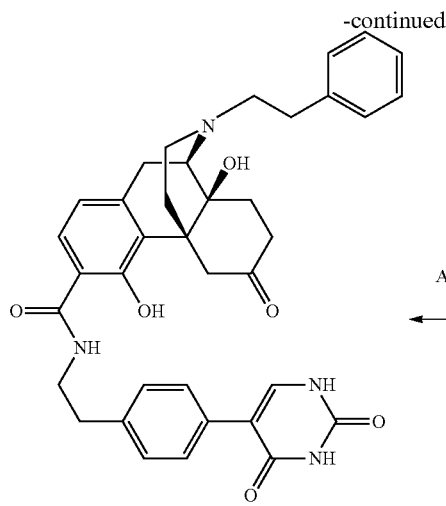

Compound 2

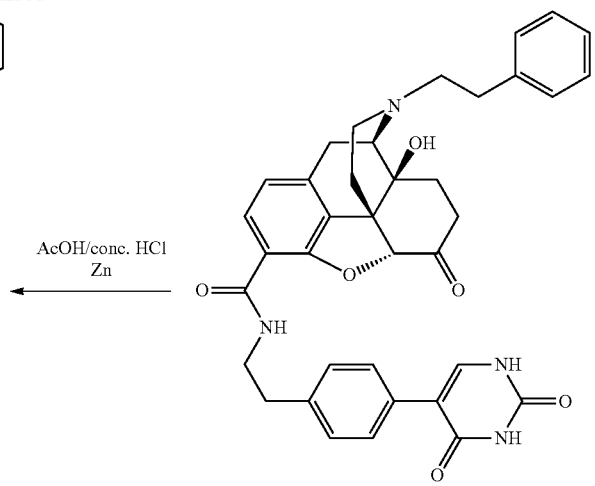

Compound 18

A mixture of Noroxymorphone (40.0 g, 139.2 mmol), potassium hydrogen carbonate (27.9 g, 278.7 mmol), and (2-bromoethyl)benzene (47.6 mL, 348.0 mmol) in DMF (750 mL) was heated at 70° C. overnight. The reaction mixture was cooled to room temperature, filtered, and concentrated under reduced pressure. The residue was partitioned between ethyl acetate (800 mL) and water (500 mL). The organic phase was dried (MgSO$_4$), filtered and the solvent removed under reduced pressure. To the crude residue was stirred with a mixture of 2NHC$_{(aq)}$ (500 mL) and ethyl acetate (500 mL). The resultant precipitate was isolated by filtration, washed with water and dried (50° C.) giving (4R,4aS,7aR,12bS)-4a,9-dihydroxy-3-phenethyl-2,3,4,4a,5,6-hexahydro-1H-4,12-methanobenzofuro[3,2-e]isoquinolin-7(7aH)-one hydrochloride (46.6 g, 109.0 mmol, 78% yield).

To a suspension of (4R,4aS,7aR,12bS)-4a,9-dihydroxy-3-phenethyl-2,3,4,4a,5,6-hexahydro-1H-4,12-methanobenzofuro[3,2-e]isoquinolin-7(7aH)-one hydrochloride (46.6 g, 109.0 mmol) in DCM (1 L) was added diisopropylethylamine (76 mL, 435.9 mmol) followed by N-phenylbis(trifluoromethanesulfonamide) (40.1 g, 112.2 mmol). The reaction was stirred at room temperature overnight. The solvent was removed under reduced pressure and the residue dissolved in 4:1 ethyl acetate:hexane (500 mL total). The organic phase was washed with water (6×500 mL) and dried (MgSO$_4$). Filtration and removal of the solvent under reduced pressure gave 4R,4aS,7aR,12bS)-4a-hydroxy-7-oxo-3-phenethyl-2,3,4,4a,5,6,7,7a-octahydro-1H-4,12-methanobenzofuro[3,2-e]isoquinolin-9-yl trifluoromethanesulfonate (57.0 g, 109.0 mmol, 100% yield) as an orange oil.

4R,4aS,7aR,12bS)-4a-hydroxy-7-oxo-3-phenethyl-2,3,4,4a,5,6,7,7a-octahydro-1H-4,12-methanobenzofuro[3,2-e]isoquinolin-9-yl trifluoromethanesulfonate (6.26 g, 12.0 mmol) was stirred in degassed DMSO (80 mL). N-hydroxysuccinimide (2.76 g, 24.0 mmol) was added followed by triethylamine (3.34 mL, 24.0 mmol), palladium acetate (269 mg, 1.2 mmol) and xantphos (693 mg, 1.2 mmol). The reaction mixture was stirred at 70° C. under an atmosphere of CO overnight. The mixture was allowed to return to room temperature before the addition of 5-(4-(2-aminoethyl)phenyl) pyrimidine-2,4(1H,3H)-dione hydrochloride (2.0 g, 8.0 mmol) and triethylamine (1.7 mL, 12.0 mmol). The reaction was stirred for 3 hours before removal of the DMSO under reduced pressure. The residue was subject to column chromatography (0 to 3% MeOH(NH$_3$) in DCM). The organic phases were combined and the solvent removed under reduced pressure giving (5a)-N-{2-[4-(2,4-dioxo-1,2,3,4-tetrahydropyrimidin-5-yl)phenyl]ethyl}-14-hydroxy-6-oxo-17-(2-phenylethyl)-4,5-epoxymorphinan-3-carboxamide (Compound 18; 4.7 g, 7.4 mmol, 62% yield).

To a solution of N-{2-[4-(2,4-dioxo-1,2,3,4-tetrahydropyrimidin-5-yl)phenyl]ethyl}-14-hydroxy-6-oxo-17-(2-phenylethyl)-4,5-epoxymorphinan-3-carboxamide (Compound 18) (4.7 g, 7.4 mmol) in acetic acid (200 mL) was added zinc powder (14.6 g, 223 mmol) followed by concentrated HCl$_{(aq)}$ (8 mL). The reaction was heated at 90° C. for 1 hour after which time further zinc powder (14.6 g) was added. The reaction was maintained at the same temperature for an additional 2 hours. The reaction mixture was allowed to cool and filtered. The zinc residue was washed with further acetic acid (100 mL). The combined acetic acid solutions were concentrated under reduced pressure. The residue was basified with ammonium hydroxide solution (28%) and the precipitated solid isolated by filtration. The precipitate was washed with water and dried overnight in a dessicator. The material was purified by prep-HPLC to give Compound 2 N-{2-[4-(2,4-Dioxo-1,2,3,4-tetrahydropyrimidin-5-yl)phenyl]ethyl}-4,14-dihydroxy-6-oxo-17-(2-phenylethyl)morphinan-3-carboxamide (1.17 g, 1.85 mmol, 25% yield) as a white solid; LC/MS 635 (M+H)$^+$; NMR (DMSO-D$_6$): 502-133-9__1H-3.jdf: 1.40-1.50 (1H, m), 1.60-1.70 (2H, m), 1.78-1.95 (3H, m), 2.50-2.58 (2H, m), 2.59-2.67 (3H, m), 2.68-2.77 (3H, m), 2.78-2.90 (4H, m), 2.91-3.20 (2H, m), 3.77 (1H, d), 4.30 (1H, s), 6.61 (1H, d), 7.10-7.32 (7H, m), 7.44 (2H, d), 7.54 (2H, d), 8.91 (1H, t), 11.07 (1H, bs), 11.20 (1H, bs), 13.94 (1H, bs).

Example 15

Determination of Binding Affinities for Mu, Delta and Kappa Receptors

Receptor Binding (in vitro Assay) The K$_i$ (binding affinity) for μ-, δ-, and κ-receptors was determined with a previously described method using a competitive displacement assay (Neumeyer, 2003). Membrane protein from CHO (Chinese Hamster Ovarian) cells that stably expressed one type of the cloned human opioid receptor were incubated with 12 different concentrations of the compound in the presence of 0.25 nM [3H]DAMGO, 0.2 nM [3H]naltrindole or 1 nM [3H]U69,593 in a final volume of 1 mL of 50 mM Tris-HCl, pH 7.5 at 25° C. Incubation times of 60 min were used for [3H] DAMGO and [3H]U69,593. Because of a slower association of [3H]naltrindole with the receptor, a 3 h incubation was used with this radioligand. Samples incubated with [3H]naltrindole also contained 10 mM $MgCl_2$ and 0.5 mM phenylmethylsulfonyl fluoride. Nonspecific binding was measured by inclusion of 10 μM naloxone. The binding was terminated by filtering the samples through Schleicher & Schuell No. 32 glass fiber filters using a Brandel 48-well cell harvester. The filters were subsequently washed three times with 3 mL of cold 50 mM Tris-HCl, pH 7.5, and were counted in 2 mL Ecoscint A scintillation fluid. For [3H]naltrindole and [3H] U69,593 binding, the filters were soaked in 0.1% polyethylenimine for at least 60 min before use. $IC_{50}$ values will be calculated by least squares fit to a logarithm-probit analysis. Ki values of unlabelled compounds were calculated from the equation Ki=(IC50)/1+S where S=(concentration of radioligand)/(Kd of radioligand) (Cheng and Prusoff, 1973).

Example 16

Functional Activity (GTPγS Binding)

The [$^{35}$S]GTPγS assay measures the functional properties of a compound by quantifying the level of G-protein activation following agonist binding in studies using stably transfected cells, and is considered to be a measure of the efficacy of a compound. Membranes from CHO (Chinese Hamster Ovary) cells that stably expressed the cloned human Mu opioid receptor were used in the experiments. In a final volume of 0.5 mL, 12 different concentrations of each test compound were incubated with 7.5 μg of CHO cell membranes that stably expressed the human μ opioid receptor. The assay buffer consisted of 50 mM Tris-HCl, pH 7.4, 3 mM $MgCl_2$, 0.2 mM EGTA, 3 μM GDP, and 100 mM NaCl. The final concentration of [$^{35}$S]GTPγS was 0.080 nM. Nonspecific binding was measured by inclusion of 10 μM GTPγS. Binding was initiated by the addition of the membranes. After an incubation of 60 min at 30° C., the samples were filtered through Schleicher & Schuell No. 32 glass fiber filters. The filters were washed three times with cold 50 mM Tris-HCl, pH 7.5, and were counted in 2 mL of Ecoscint scintillation fluid. Data are the mean Emax and EC50 values±S.E.M. For calculation of the Emax values, the basal [$^{35}$S]GTPγS binding was set at 0%, and the 100% [$^{35}$S]GTPγS binding level was set at the maximum binding achieved with DAMGO. Compounds in Table D show [$^{35}$S]GTPγS binding EC50 values between 1.3 nM and 300 nM with Emax values between 70% and 140%.

Example 17

In Vivo Behavioral Studies

Groups of mice (n=5 per group; >60 days; 20-25 grams weight) were dosed with vehicle (0.9% sterile saline) or test compounds (10 mg/kg free base, SC) 30 minutes before the first observation period. The occurrence of Straub tail, piloerection, hyperlocomotion, hypolocomotion, circling of the cage, sedation, breathing abnormalities, diuresis, seizure activity and occurrences of death were recorded at 0.5, 1, 2, 4, 6 and 24 hours following dosing.

The data below shows peripheral restriction for a series of compounds. This is tested with our clinical observation assay where mice are injected with 10 mg/kg subcutaneously with drug and the behaviors are noted over 24 hours. At the 10 mg/kg SC dose both morphine (Compound-A) and Compound-B show severe effects that reflect mu agonism in the brain, with observed mortality in the Compound-B group. In the heteroaryl compounds tested the behavioral effects and mortality was not observed.

The binding affinities of Compounds 1-11 are given in Table D

TABLE D

| No | Compound | Clinical Observations after 10 mg/kg subcutaneous injection | Binding affinity | | | In vitro functional agonism for |
|---|---|---|---|---|---|---|
| | | | μ ($K_i$, nm) | κ ($K_i$, nm) | δ ($K_i$, nm) | μ receptor Agonist? |
| A | 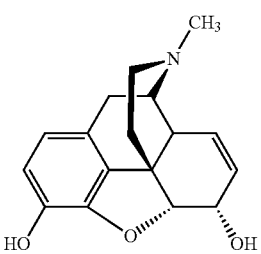 | Multiple central nervous system like effects: Straub tail, hyperlocomotion, circling | 0.32 | 230 | 11 | Yes |

TABLE D-continued

| No | Compound | Clinical Observations after 10 mg/kg subcutaneous injection | Binding affinity μ (K$_i$, nm) | κ (K$_i$, nm) | δ (K$_i$, nm) | In vitro functional agonism for μ receptor Agonist? |
|---|---|---|---|---|---|---|
| B | (structure) | Angioedema; Straub tail, hypolocomotion, mortality | 0.39 | 0.71 | 5.4 | Yes |
| 1 | (structure) | None | 27 | 850 | 490 | Yes |
| 2 | (structure) | None | 0.66 | >1 uM | 24 | Yes |

TABLE D-continued

| No | Compound | Clinical Observations after 10 mg/kg subcutaneous injection | Binding affinity | | | In vitro functional agonism for |
|---|---|---|---|---|---|---|
| | | | μ ($K_i$, nm) | κ ($K_i$, nm) | δ ($K_i$, nm) | μ receptor Agonist? |
| 3 | | None | 0.63 | 180 | 17 | Yes |
| 4 | | None | 1.3 | 190 | >1 uM | Yes |
| 5 | | None | 1.7 | 680 | 51 | Yes |
| 6 | | None | 3.5 | 1000 | 97 | Yes |

TABLE D-continued

| No | Compound | Clinical Observations after 10 mg/kg subcutaneous injection | Binding affinity μ (K$_i$, nm) | κ (K$_i$, nm) | δ (K$_i$, nm) | In vitro functional agonism for μ receptor Agonist? |
|---|---|---|---|---|---|---|
| 7 | (structure) | None | 0.52 | 860 | 42 | Yes |
| 8 | (structure) | None | 0.15 | 19 | 2.1 | Yes |
| 9 | (structure) | None | 1.7 | 400 | 280 | Yes |
| 10 | (structure) | None | 0.43 | 140 | 10 | Yes |

TABLE D-continued

| No | Compound | Clinical Observations after 10 mg/kg subcutaneous injection | Binding affinity μ (K$_i$, nm) | Binding affinity κ (K$_i$, nm) | Binding affinity δ (K$_i$, nm) | In vitro functional agonism for μ receptor Agonist? |
|---|---|---|---|---|---|---|
| 11 | [structure] | None | 1.6 | | >1 uM | Yes |

Example 18

CFA Induced Weight Bearing Deficits in Rats

Animals were habituated to the weight bearing test apparatus for 2 days prior to the start of the experiment. On Day 0, rats were tested in the weight bearing apparatus to measure baseline weight bearing of untreated hind paws. Following baseline testing, animals were injected intra-plantar with Complete Freund's Adjuvant (CFA). Using a syringe with a locking hub and 25 G needle, rats were injected via rear, left intra-plantar administration with 100 μL of 100% CFA (1.0 mg/ml) while under light isofluorane anesthesia. No treatment was administered to the right, rear, contralateral paw.

The treatment with morphine or Compound 4 (Intra-articular) was given after at the onset of arthritis in CFA treated rats (Day 1). Intra-plantar test-compound administration was done while the animal was under light (3%) isofluorane anesthesia using 0.3 ml insulin syringe. The amount of anesthesia given to the animal during test compound administration was limited to a very short duration, so not to impede measurement of weight bearing at the 5 minute time point. On Day 1 (24 hrs post CFA), rats were tested in the weight bearing apparatus to measure CFA-induced changes in weight bearing. Following testing, animals were injected intra-plantar with test compound (morphine or Compound 4) in a total volume of 50 μl containing 3, 10 or 100 μg doses. The inhibitory effect of naloxone on the analgesic effects of Compound 4 and morphine (10 μg/paw) was tested by concurrent intra-plantar administration of 75 ug naloxone methiodide, a peripherally restricted opioid antagonist. Following test compound administration, animals were retested in the weight bearing apparatus at the following time points: 5, 15, 30, 60 and 120 minutes post-test compound administration. Animals were retested on Day 2 (post-CFA) if there is a significant change in CFA induced weight bearing at the 120 minute time point on Day 1.

Figure 2:
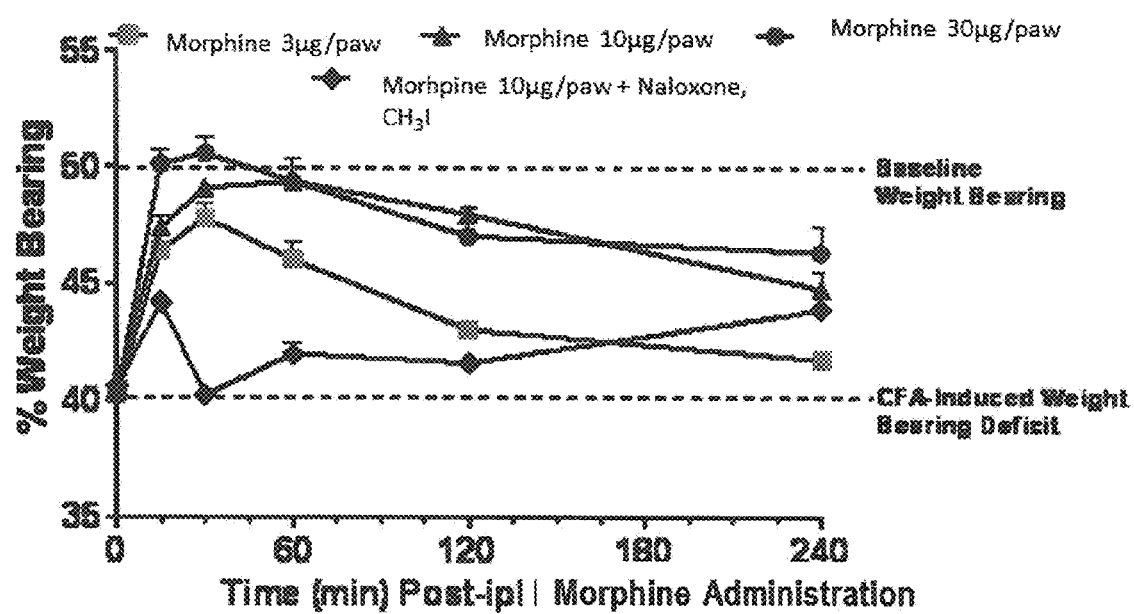
FIG. 2: The administration (intra-plantar) of morphine produced a dose-dependent reversal of CFA-induced weight bearing deficits at 3, 10 and 30 μg/paw.

The administration (intra-plantar) of Compound 4 produced a dose-dependent reversal of CFA-induced weight bearing deficits at 3, 10 and 30 μg/paw. The analgesic effects of Compound 4, was comparable to that seen with Morphine (FIGS. 1 and 2). The analgesic effects of Compound 4 or Morphine (10 μg/paw) are significantly inhibited by concurrent intra-plantar administration of 75 ug naloxone methiodide, a peripherally restricted opioid antagonist. The blockade of analgesia by intraplantar naloxone methiodide administration is suggestive of peripheral analgesic effects of Compound 4 and morphine.

Example 19

Rat Hot Plate Model of Centrally Mediated Analgesia

The potential antinociceptive properties of subcutaneous (SC) administration of Compound 4 were assessed at doses of 10, 30, and 100 mg/kg in the rat hot plate test of antinociception. Morphine (used as a reference compound) produced maximal (60 sec) antinociception when administered SC at 7.5 mg/kg (shown here, and in previous in-house experiments).

Rats were tested for a baseline hot plate response (latency time for a paw on a hot plate set to 52.5° C.) immediately prior to dosing with Compound 4 or morphine (7.5 mg/kg) by SC injection. Rats were then tested on the hot plate 5, 30, 60, 120, 240 and 360 minutes later. The amount of time it took to lick one hind paw is measured and is considered the response latency. The mean and SEM of the responses latencies for each experimental group were calculated and a line depicting mean hot plate latency vs. time was generated using GraphPad Prism. An increase in mean response latency above baseline following test compound administration is indicative of an antinociceptive effect.

Figure 3:
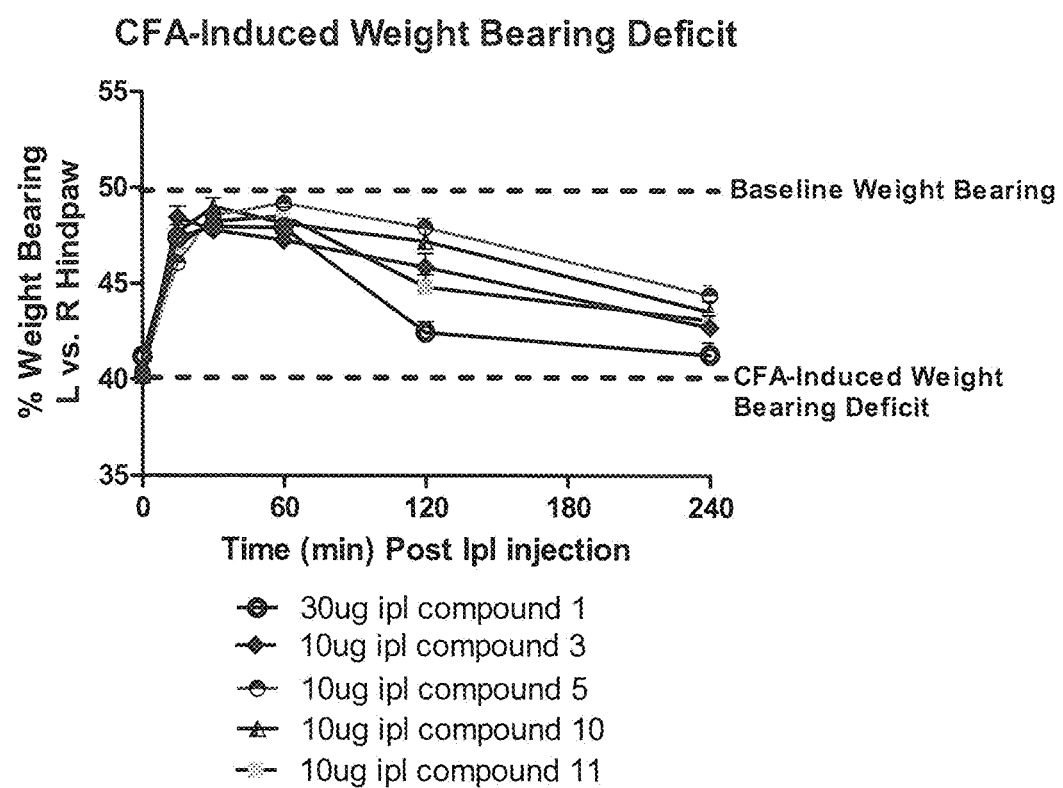
FIG. 3: The antinociceptive properties of subcutaneous (SC) administration of Compound 4 were assessed at doses of 10, 30, and 100 mg/kg in the rat hot plate test of antinociception.

Compound 4 was significantly less active than morphine in hot plate, with sub-maximal efficacy at the highest dose tested (100 mg/kg), suggesting significant peripheral restriction of Compound 4 (FIG. 3).

Example 20

Formalin Model of Pain

Nonfasted male Harlan rats were assigned to treatment group according to a randomized block study design to balance for test chamber and time of day, and day of test (if applicable). Each rat was administered either vehicle or test compound subcutaneously and then placed in their assigned test chamber and acclimated for 25-30 minutes with the chamber enclosure door left open. Data was not collected during this period. Following the acclimation period, each rat was removed individually starting with chamber 1, and dosed 5% formalin subcutaneously into the right rear paw plantar surface (formalin was made from a 37% stock solution, diluted down to 5% with saline).

Data collection started when the first rat was replaced in chamber 1 and the chamber door was closed and latched (skipped 1-minute acclimation screen on software). The number of events (also defined as "number of seconds"), defined as the number of 1-second bins with a change in dynamic force that exceeded an empirically determined threshold value (a value of arbitrary load units, which corresponded visually with rats quietly breathing or sniffing), were totaled in 5-minute intervals. In control rats, the number of events first increases within 5 minutes and then decreases during the subsequent 5 minutes (a quiescent phase) after formalin administration (Phase I, or Early Phase, of the formalin test), then increases again during the subsequent 35 minutes (Phase II, or Late Phase) of the formalin test. Formalin-induced movements detected by the system include licking and flinching of the affected paw as well as hopping and turning.

For constructing summaries for analysis of dose response curves or screens in the formalin test, the total number of events during the first 5 minutes after formalin administration was considered to be Phase I (Early Phase), and the total number of events for minutes 11 to 35 after formalin was considered to be Phase II (Late Phase). Data were analyzed using 1-way ANOVA, and comparisons of drug treatment groups were compared with control groups using appropriate, statistician-guided tests—most commonly Dunnett's for dose response curves and a Student's t-test for two-group (i.e. vehicle vs. positive control) comparison—utilizing JMP statistical software (SAS Institute Inc, Cary, N.C.). Data was expressed as means±SEM. An $ED_{50}$ was calculated utilizing GraphPad Prism software.

Figure 4:
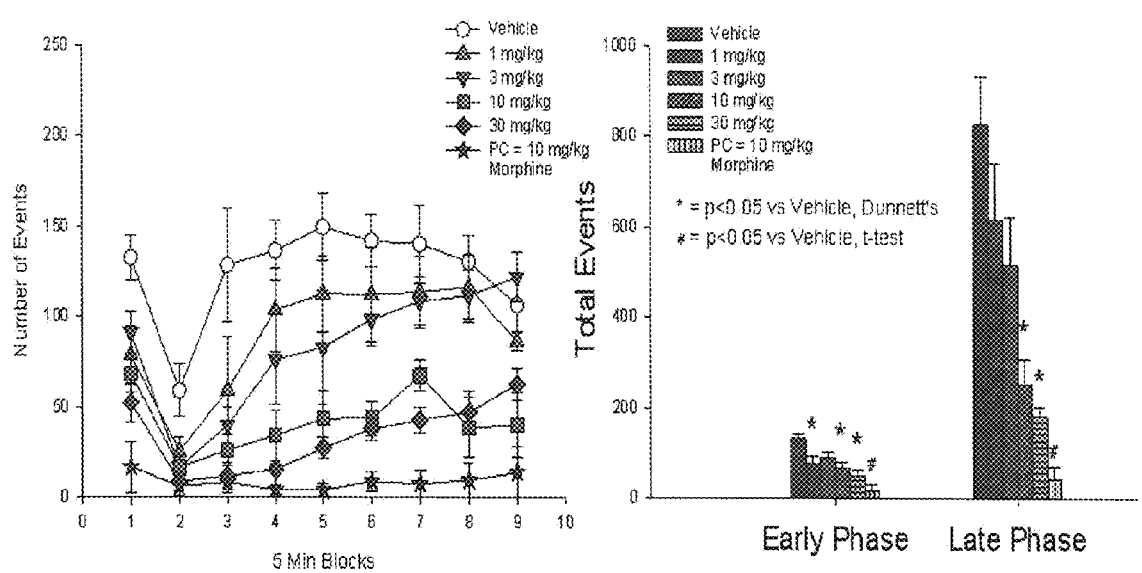
FIG. 4: Subcutaneous administration of Compound 4 produced a dose-dependent reversal of formalin-induced events in a formalin model of pain.

Subcutaneous administration of Compound 4 produced a dose-dependent reversal of formalin-induced events. The antinociceptive (analgesic) effects of Compound 4 ($ED_{50}$ 3.62 mg/kg) were comparable to morphine ($ED_{50}$ 2.4 mg/kg). As shown in FIG. 4, a 10 mg/kg dose of morphine completely mitigates both the early and late phase effects of formalin, suggesting both a centrally mediated (Early Phase) and peripherally mediated (Late Phase) effect on antinociception (analgesia). There is a more robust effect of Compound 4 in the Late Phase effects than the Early Phase, suggesting a preferential, peripherally mediated effect on peripheral inflammatory pain.

Example 21

Acetic-Acid Induced Writhing Model of Inflammatory Pain

Intraperitoneal administration of morphine dose-dependently blocks writhing induced by the intraperitoneal administration of 1% acetic acid in mice with an $ED_{50}$ of 0.25 mg/kg. A dose response of the analgesic effects of intraperitoneal administration of Compound 4 in the 1% acetic acid induced writhing assay in mice was measured.

Groups of mice (n=10 per group) were dosed intraperitoneally with a vehicle control (0.9% saline), morphine or Compound 4, 30 minutes before testing followed by a dose of 1% acetic acid 5 minutes before testing. The number of writhes was counted for 15 minutes (3 consecutive 5 minute time bins). In order for a movement to be considered a writhe, two or more of the following criteria were met:

A perceivable concave curvature of the spine (termed a pelvic tilt)-dorsal movement of the caudal spine region creating a concave shape when viewed from the side; movement of the hips to either the left or the right; or both.

A more severe concave spinal curvature was considered a vertical writhe.

Abdomen made an effort to lower to the ground.

Hind legs, body, or both extended backwards and lengthened.

Tail flicked upward from base (does not typically occur separate from pelvic tilt).

In the event of a chain of multiple writhes, the end of a discrete writhe was determined when the mouse returned to "normal" posture before writhing once again. "Normal" posture was defined as movements opposite to those listed above (e.g. convex curvature of the spine, legs not extended, abdomen not lowered, tail in a straight or relaxed position, etc).

The total number of writhes over the 15 minute test session was used for all data analysis. All data was transformed using GraphPad Prism to % change from daily vehicle control for analysis based on the number of writhes produced by the saline vehicle control group (% change=# writhes in test group/mean # of writhes in daily vehicle control group*100). An $ED_{50}$ of the % change from daily vehicle control was calculated for morphine and compound 4 utilizing GraphPad Prism software.

Figure 5:
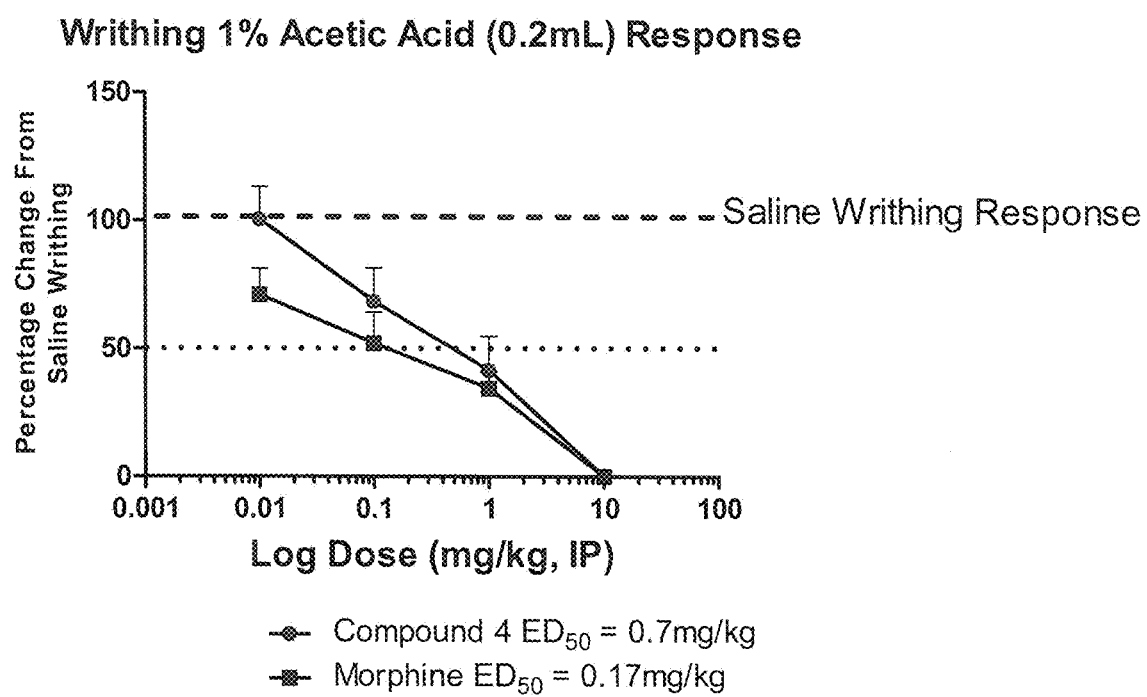
FIG. 5: Administration (intraperitoneal) of Compound 4 blocked acetic acid induced writhing in a dose-dependent manner in an acetic-acid induced writhing model of inflammatory pain.

As shown in FIG. 5, administration (intraperitoneal) of Compound 4 blocked acetic acid induced writhing in a dose-dependent manner with a calculated $ED_{50}$ of 0.7 mg/kg.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A compound of Formula I, II, III, IV or a pharmaceutically acceptable salt thereof:

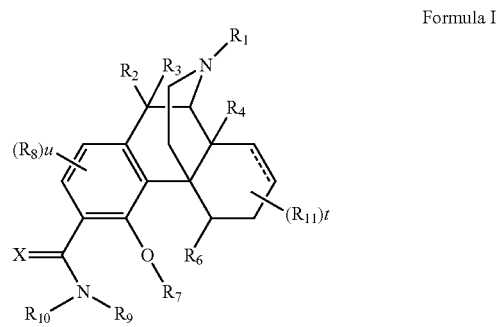

Formula I

-continued

Formula II

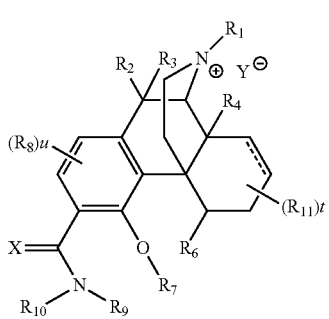

Formula III

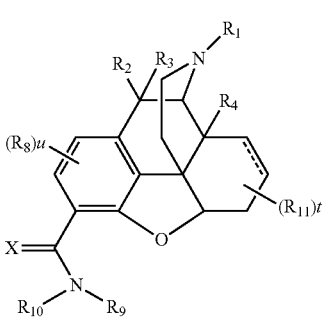

Formula IV

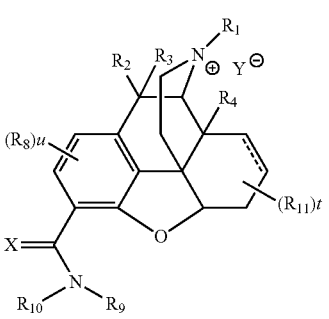

Wherein:
u is 0, 1 or 2;
t is 0, 1, 2, 3, 4, 5, or 6;
X is S or O;
$Y^{\ominus}$ is a pharmaceutically acceptable counterion;
$R_1$ is selected from aliphatic, substituted aliphatic, aryl, substituted aryl, heterocyclyl or substituted heterocyclyl;
Each $R_2$, $R_3$, $R_4$, $R_6$, $R_8$, and $R_{11}$ is independently selected from hydrogen, halogen, $-OR_{20}$, $-SR_{20}$, $-NR_{20}R_{21}$, $-C(O)R_{20}$, $-C(O)OR_{20}$, $-C(O)NR_{20}R_{21}$, $-N(R_{20})C(O)R_{21}$, $-CF_3$, $-CN$, $-NO_2$, $-N_3$, acyl, alkoxy, substituted alkoxy, alkylamino, substituted alkylamino, dialkylamino, substituted dialkylamino, alkylthio, substituted alkylthio, alkylsulfonyl, substituted alkylsulfonyl, aliphatic, substituted aliphatic, aryl, substituted aryl, heterocyclyl or substituted heterocyclyl; or alternatively, $R_4$, and $R_{11}$ together with the atoms they are attached form one optionally substituted rings; alternatively $R_2$ and $R_3$ together with the carbon they are attached to form a C=X group or a vinyl group; alternatively, two $R_{11}$ groups together with the carbon atom to which they are attached form a C=X or a vinyl group; wherein each $R_{20}$ and $R_{21}$ is independently selected from hydrogen, halogen, -alkyl, substituted alkyl, aryl or substituted aryl;
$R_5$ is alkyl, substituted alkyl, aryl or substituted aryl;
$R_7$ is hydrogen, alkyl, substituted alkyl, aryl or substituted aryl;
$R_9$ is selected from hydrogen, aliphatic, substituted aliphatic, aryl, substituted aryl, heterocyclyl or substituted heterocyclyl;
$R_{10}$ is selected from Table A;

TABLE A

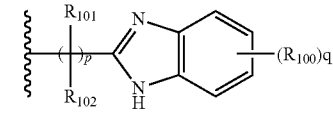

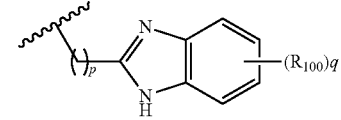

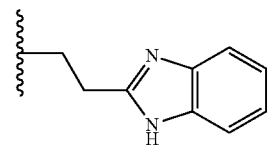 [SMILES: *CCc1nc2ccccc2[nH]1]

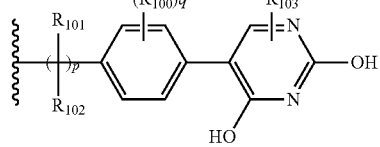

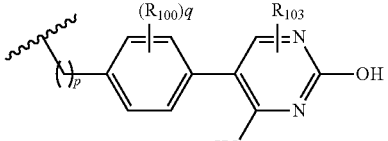

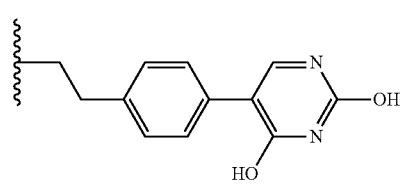 [SMILES: *CCc1ccc(-c2cnc(O)nc2O)cc1]

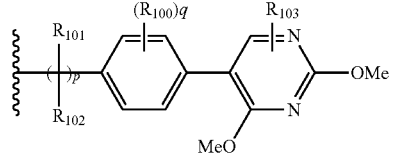

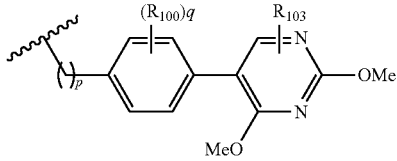

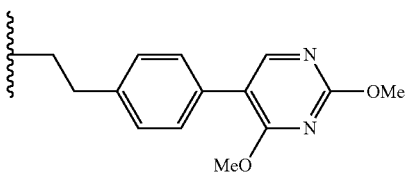

TABLE A-continued
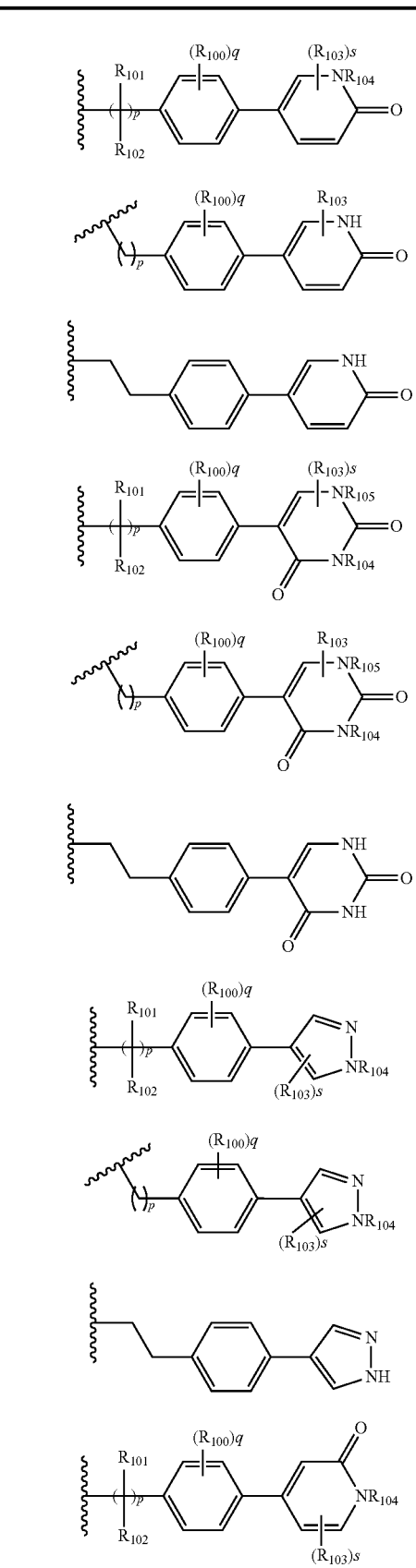
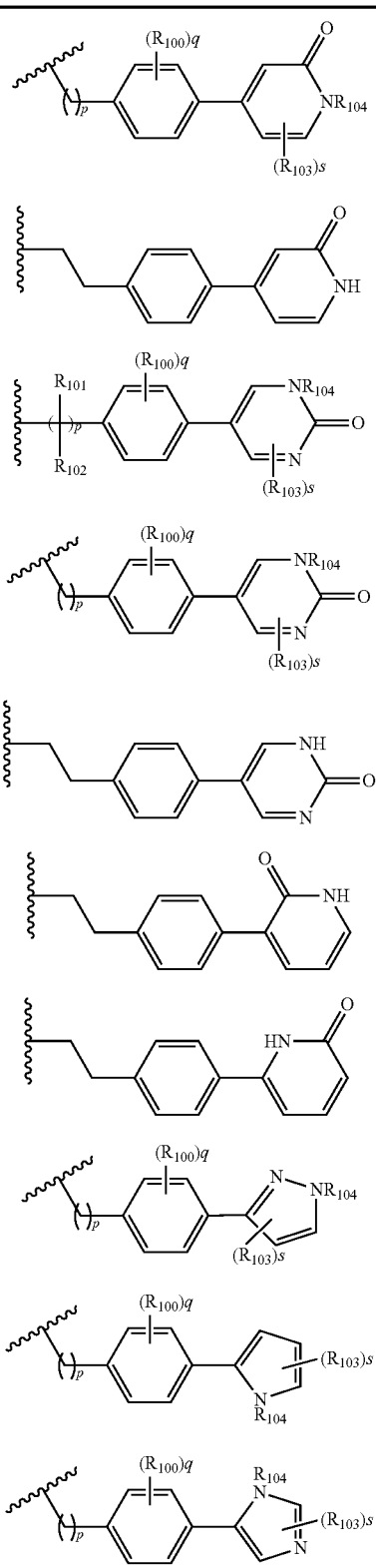
Wherein s is 0, 1, 2, or 3;
p is 0, 1, 2, 3, 4, 5, 6, or 7;
q is 0, 1, 2, 3, 4, or 5;
Each $R_{100}$, $R_{101}$, $R_{102}$, $R_{103}$, $R_{104}$, and $R_{105}$ is independently selected from hydrogen, halogen, —$OR_{20}$, —SR$_{20}$, —NR$_{20}$R$_{21}$, —C(O)R$_{20}$, —C(O)OR$_{20}$, —C(O)NR$_{20}$R$_{21}$, —N(R$_{20}$)C(O)R$_{21}$, —CF$_3$, —CN, —NO$_2$, —N$_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, optionally substituted aliphatic, optionally substituted aryl, heterocyclyl or substituted heterocyclyl.

2. A compound of Formula V or VI, or a pharmaceutically acceptable salt thereof:

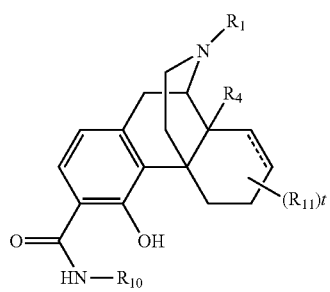

Formula V

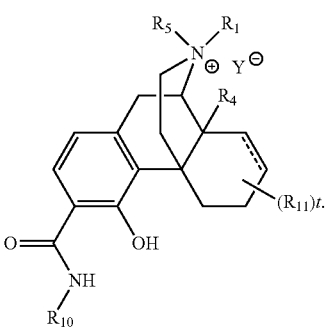

Formula VI

Wherein t is 0, 1, 2, 3, or 4;

Y$^\ominus$ is a pharmaceutically acceptable counterion;

R$_1$ is selected from aliphatic, substituted aliphatic, aryl, substituted aryl, heterocyclyl or substituted heterocyclyl;

Each R$_4$ and R$_{11}$ is independently selected from hydrogen, halogen, —OR$_{20}$, —SR$_{20}$, —NR$_{20}$R$_{21}$, —C(O)R$_{20}$, —C(O)OR$_{20}$, —C(O)NR$_{20}$R$_{21}$, —N(R$_{20}$)C(O)R$_{21}$, —CF$_3$, —CN, —NO$_2$, —N$_3$, acyl, alkoxy, substituted alkoxy, alkylamino, substituted alkylamino, dialkylamino, substituted dialkylamino, alkylthio, substituted alkylthio, alkylsulfonyl, substituted alkylsulfonyl, aliphatic, substituted aliphatic, aryl, substituted aryl, heterocyclyl or substituted heterocyclyl; or alternatively two R$_{11}$ groups together with the carbon atom to which they are attached form a C=X or a vinyl group;

wherein each R$_{20}$ and R$_{21}$ is independently selected from hydrogen, halogen, alkyl, substituted alkyl, aryl or substituted aryl;

X is S or O;

R$_5$ is alkyl, substituted alkyl, aryl or substituted aryl;

R$_7$ is hydrogen, alkyl, substituted alkyl, aryl or substituted aryl;

R$_9$ is selected from hydrogen, aliphatic, substituted aliphatic, aryl, substituted aryl, heterocyclyl or substituted heterocyclyl;

R$_{10}$ is selected from Table A:

TABLE A

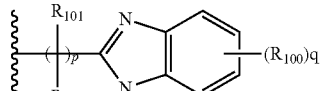

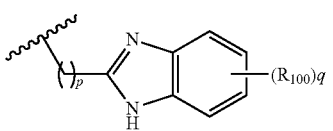

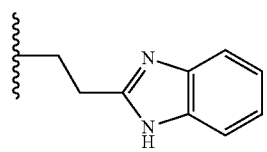 [SMILES: *CCc1nc2ccccc2[nH]1]

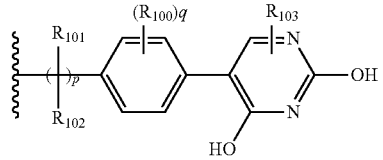

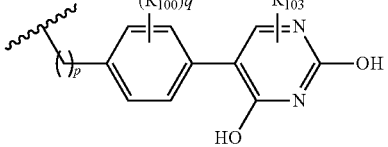

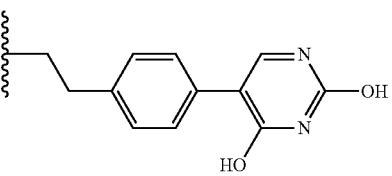 [SMILES: *CCc1ccc(-c2cnc(O)nc2O)cc1]

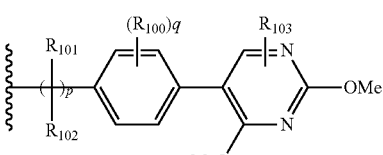

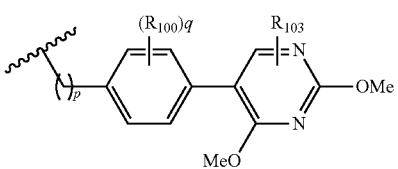

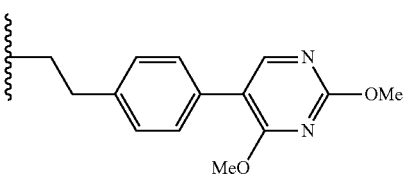 [SMILES: *CCc1ccc(-c2cnc(OC)nc2OC)cc1]

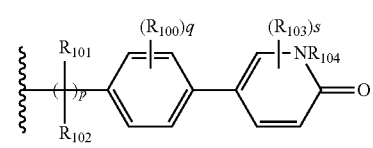

TABLE A-continued

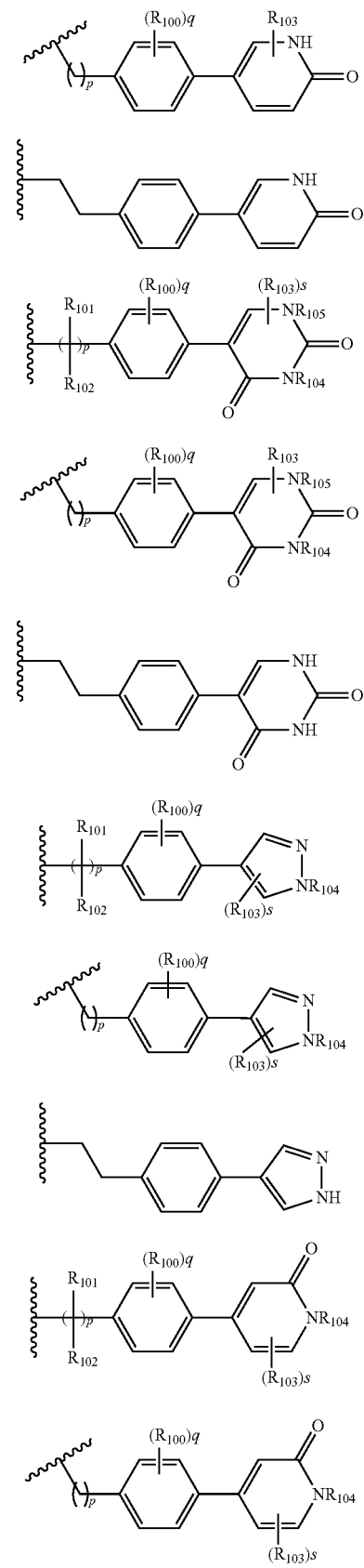

TABLE A-continued

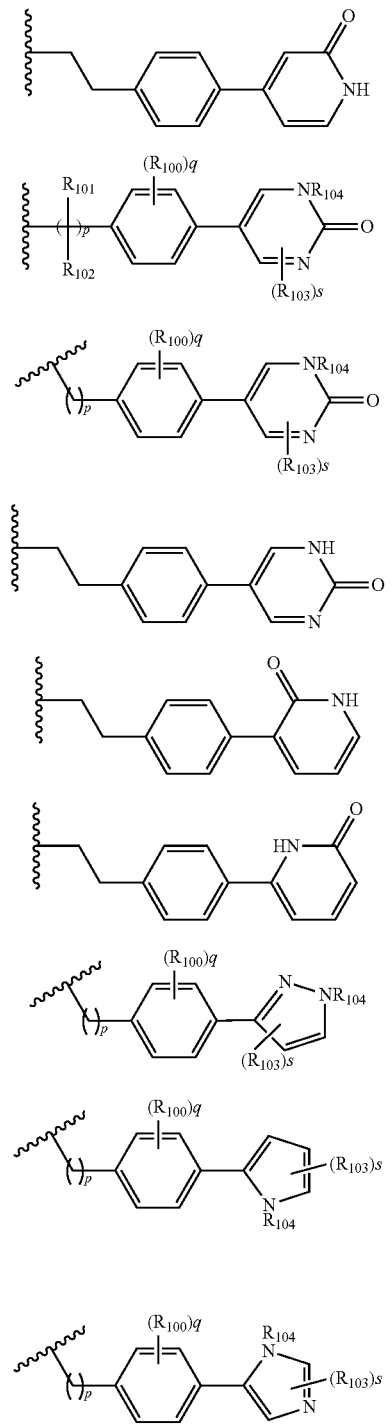

Wherein s is 0, 1, 2, or 3;
p is 0, 1, 2, 3, 4, 5, 6, or 7;
q is 0, 1, 2, 3, 4, or 5;
Each $R_{100}$, $R_{101}$, $R_{102}$, $R_{103}$, $R_{104}$, and $R_{105}$ is independently selected from hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, optionally substituted aliphatic, optionally substituted aryl, heterocyclyl or substituted heterocyclyl.
3. A compound according to claim 1 selected from Table B:
TABLE B
| No | Compound |
|----|----------|
| 1. | 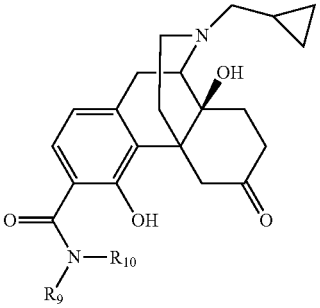 |
| 2. | 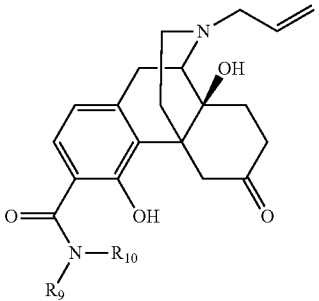 |
| 3. | 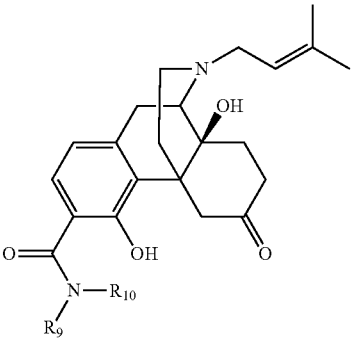 |
| 4. | 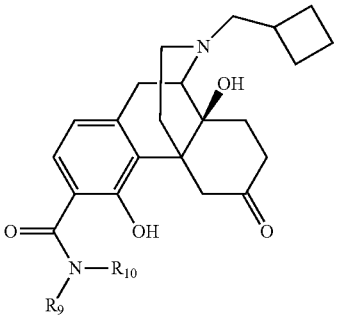 |
TABLE B-continued
| No | Compound |
|----|----------|
| 5. | 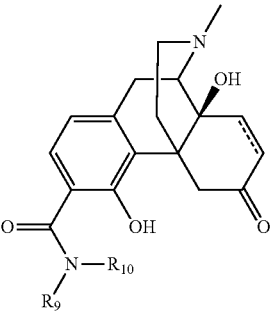 |
| 6. | 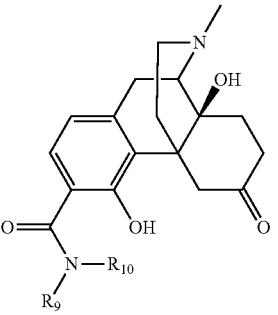 |
| 7. | 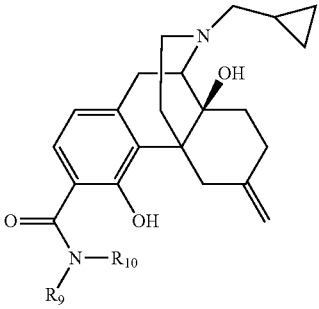 |
| 8. | 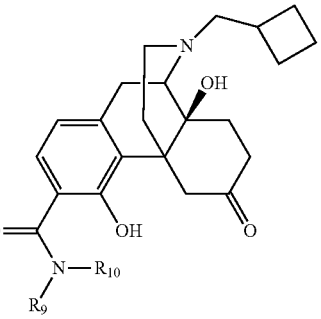 |
| 9. | 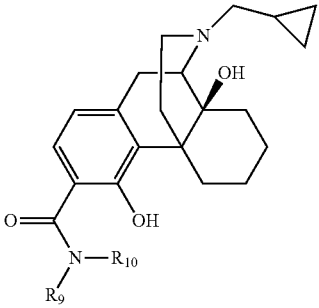 |

TABLE B-continued

| No | Compound |
|----|----------|
| 10. | (structure with cyclobutylmethyl N-substituent, OH, OH, and C(O)N(R9)R10) |
| 11. | (structure with cyclopropylmethyl N-substituent, tert-butyl, OMe, OH, and C(O)N(R9)R10) |
| 12. | (structure with cyclopropylmethyl N-substituent, alkene, tert-butyl, OMe, OH, and C(O)N(R9)R10) |
| 13. | (structure with cyclopropylmethyl N-substituent, OH, NHC(O)CH=CHCO2Me, and C(O)N(R9)R10) |
| 14. | (structure with N-Me, OMe, ketone, OH, and C(O)N(R9)R10) |
| 15. | (structure with cyclopropylmethyl N-substituent, OH, NH2, and C(O)N(R9)R10) |
| 16. | (structure with phenethyl N-substituent, OH, ketone, OH, and C(O)N(R9)R10) |

Wherein $R_9$ is selected from hydrogen, aliphatic, substituted aliphatic, aryl, substituted aryl, heterocyclyl or substituted heterocyclyl; and, $R_{10}$ is selected from Table A:

(benzimidazole structure with $R_{101}$, $R_{102}$, $(CH_2)_p$, and $(R_{100})_q$ substituents)

(benzimidazole structure with $(CH_2)_p$ linker and $(R_{100})_q$)

(benzimidazole structure with ethylene linker)

(biphenyl-pyrimidine structure with $R_{101}$, $R_{102}$, $(CH_2)_p$, $(R_{100})_q$, $R_{103}$, OH and HO substituents)

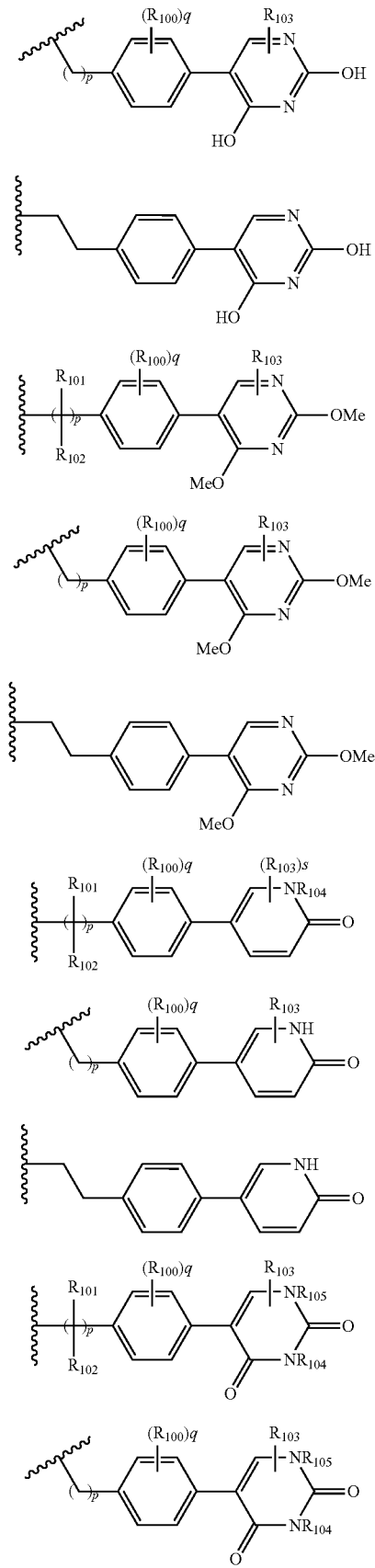
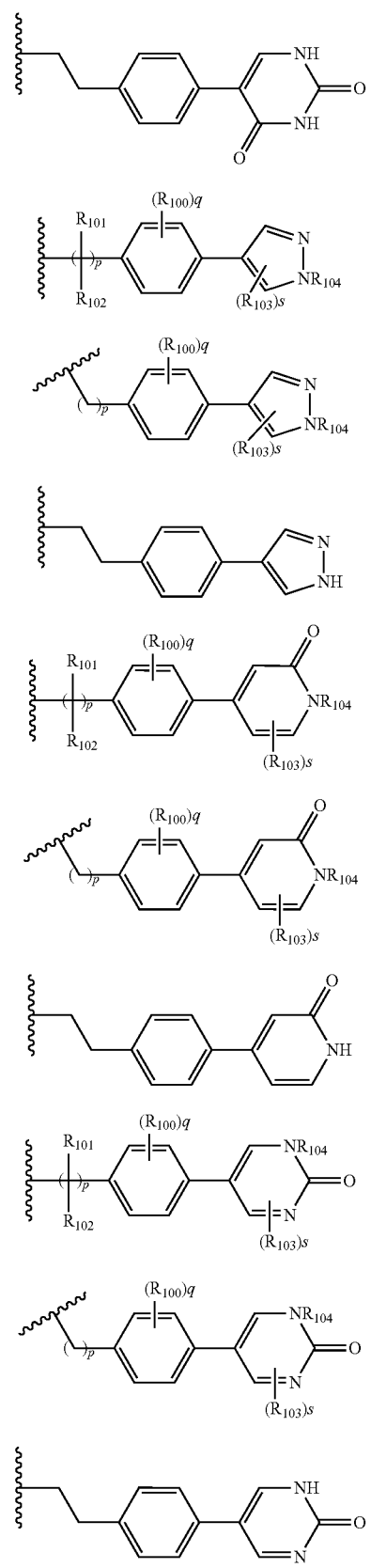

-continued

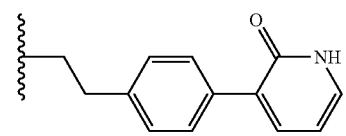

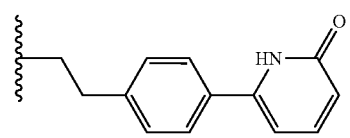

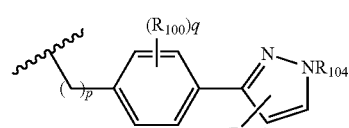

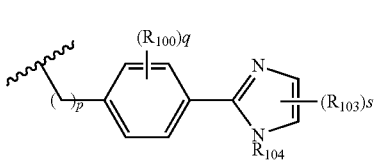

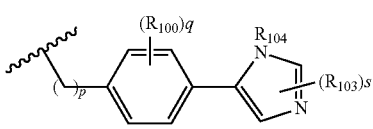

Wherein s is 0, 1, 2, or 3;

p is 0, 1, 2, 3, 4, 5, 6, or 7;

q is 0, 1, 2, 3, 4, or 5;

Each $R_{100}$, $R_{101}$, $R_{102}$, $R_{103}$, $R_{104}$, and $R_{105}$ is independently selected from hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, optionally substituted aliphatic, optionally substituted aryl, heterocyclyl or substituted heterocyclyl.

4. A compound according to claim 3 wherein $R_{10}$ is selected from:

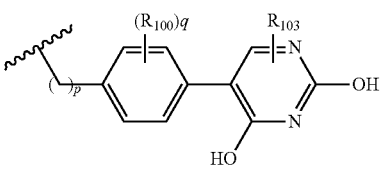

-continued

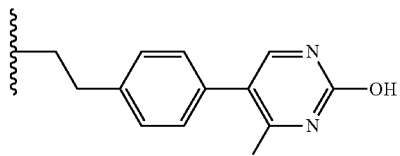

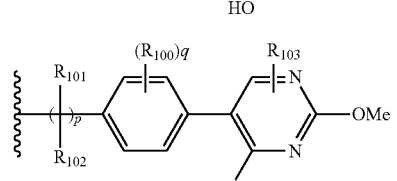

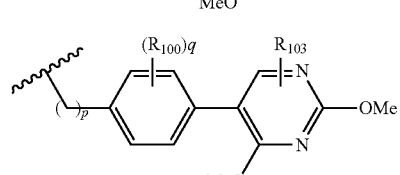

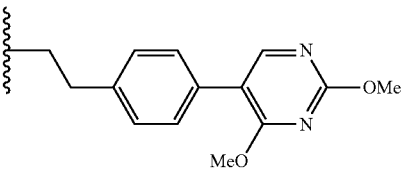

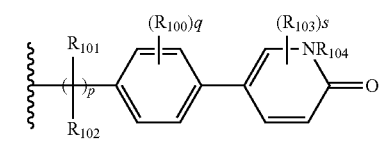

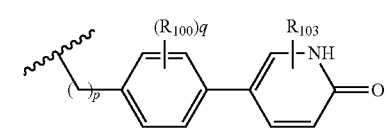

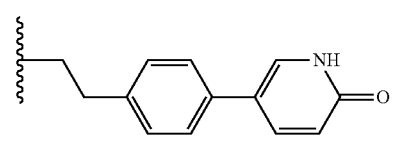

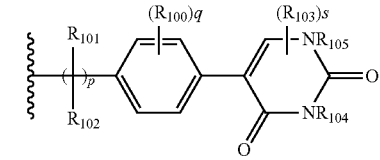

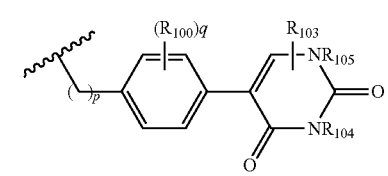

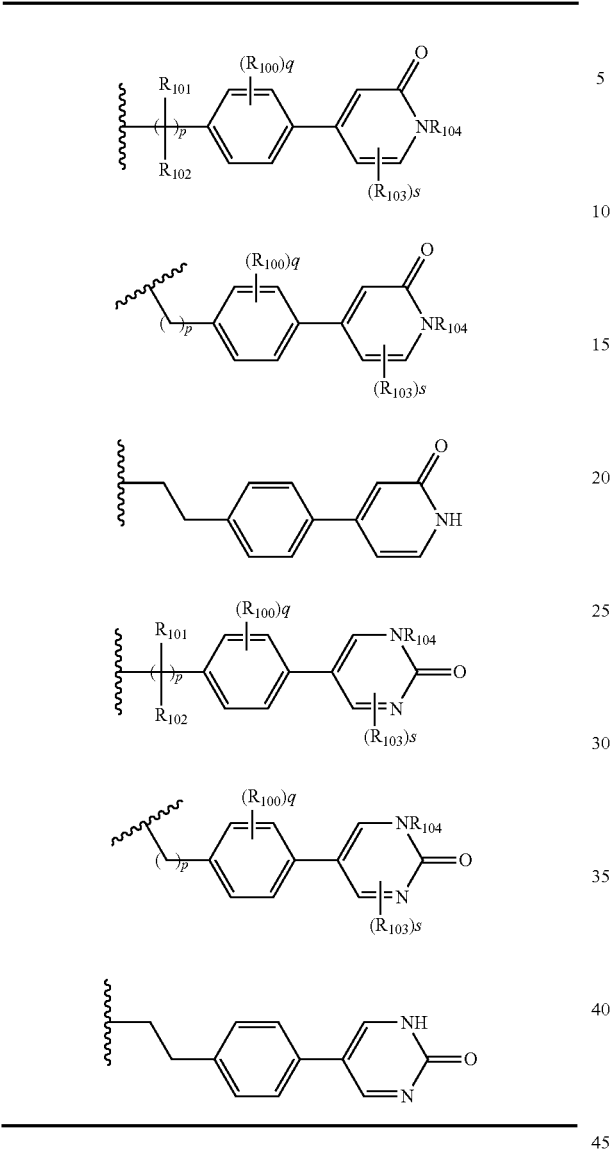

Wherein s is 0, 1, 2, or 3;

p is 0, 1, 2, 3, 4, 5, 6, or 7;

q is 0, 1, 2, 3, 4, or 5;

Each $R_{100}$, $R_{101}$, $R_{102}$, $R_{103}$, $R_{104}$, and $R_{105}$ is independently selected from hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, optionally substituted aliphatic, optionally substituted aryl, heterocyclyl or substituted heterocyclyl.

5. A compound according to claim 1 wherein $R_1$ is selected from, —$(CH_2)_a$—CH=$CH_2$, —$CH_3$, —$CH_2$—$CH_2$-Phenyl or —$(CH_2)_a$—CH=$C(CH_3)_2$ wherein a is independently 0, 1, 2 or 3.

6. A compound according to claim 1 wherein u is 1.

7. A compound according to claim 1 wherein X is oxygen.

8. A compound selected from Table C:

TABLE C

| No | Compound |
|---|---|
| 1 | |
| 2 | |
| 3 | |
| 4 | |

TABLE C-continued

| No | Compound |
|----|----------|
| 5  | |
| 6  | |
| 7  | |
| 8  | |
| 9  | |
| 10 | |
| 11 | |
| 12 | |

TABLE C-continued

| No | Compound |
|---|---|
| 13 | (structure) |
| 14 | (structure) |
| 15 | (structure) |
| 16 | (structure) |
| 17 | (structure) |
| 18 | (structure) |

* * * * *